United States Patent
Fedurco et al.

(10) Patent No.: US 10,800,795 B2
(45) Date of Patent: Oct. 13, 2020

(54) BORATED BENZOXAZINE FOR USE IN THE SYNTHESIS OF POLYBENZOXAZINE

(71) Applicant: COMPAGNIE GENERALE DES ETABLISSEMENTS MICHELIN, Clermont-Ferrand (FR)

(72) Inventors: Milan Fedurco, Clermont-Ferrand (FR); Marco Ribezzo, Clermont-Ferrand (FR)

(73) Assignee: Compagnie Generale Des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/617,650

(22) PCT Filed: May 28, 2018

(86) PCT No.: PCT/EP2018/063965
§ 371 (c)(1),
(2) Date: Nov. 27, 2019

(87) PCT Pub. No.: WO2018/219882
PCT Pub. Date: Dec. 6, 2018

(65) Prior Publication Data
US 2020/0115394 A1     Apr. 16, 2020

(30) Foreign Application Priority Data

May 31, 2017   (FR) ........................ 17 54810

(51) Int. Cl.
*C07F 5/02*   (2006.01)

(52) U.S. Cl.
CPC ................... *C07F 5/027* (2013.01)

(58) Field of Classification Search
CPC ............................................ C07F 5/027
USPC ........................................... 554/141
See application file for complete search history.

(56) References Cited

U.S. PATENT DOCUMENTS

| | | | |
|---|---|---|---|
| 5,543,516 A | 8/1996 | Ishida | |
| 7,649,060 B2 | 1/2010 | Li et al. | |
| 9,499,666 B2 | 11/2016 | Ward et al. | |
| 9,617,372 B2 | 4/2017 | Fedurco et al. | |
| 9,845,376 B2 | 12/2017 | Fedurco et al. | |
| 10,150,833 B2 | 12/2018 | Fedurco et al. | |
| 2007/0129509 A1 | 6/2007 | Li et al. | |
| 2011/0056779 A1* | 3/2011 | McGee | F16D 69/04 188/250 E |
| 2013/0267659 A1 | 10/2013 | Ward et al. | |
| 2015/0259463 A1 | 9/2015 | Fedurco et al. | |
| 2015/0274878 A1 | 10/2015 | Fedurco et al. | |
| 2016/0122460 A1 | 5/2016 | Fedurco et al. | |
| 2018/0370284 A1 | 12/2018 | Fedurco et al. | |
| 2019/0300765 A1 | 10/2019 | Fedurco et al. | |
| 2020/0087268 A1 | 3/2020 | Fedurco et al. | |
| 2020/0095211 A1 | 3/2020 | Fedurco et al. | |
| 2020/0095458 A1 | 3/2020 | Fedurco et al. | |

FOREIGN PATENT DOCUMENTS

| | | |
|---|---|---|
| JP | 2004-83623 A | 3/2004 |
| WO | 2007/064801 A1 | 6/2007 |
| WO | 2010/002872 A2 | 1/2010 |
| WO | 2013/148408 A1 | 10/2013 |
| WO | 2014/063963 A2 | 5/2014 |
| WO | 2014/063968 A1 | 5/2014 |
| WO | 2014/173838 A1 | 10/2014 |
| WO | 2014/173839 A1 | 10/2014 |

OTHER PUBLICATIONS

International Search Report dated Aug. 20, 2018, in corresponding PCT/EP2018/063965 (4 pages).
N.N. Ghosh et al., "Polybenzoxazines—New high performance thermosetting resins: Synthesis and properties", Prog. Polym. Sci. 32 (2007) 1344-1391.
Y. Yagci et al., "Recent Advancement on Polybenzoxazine—A Newly Developed High Performance Thermoset", J. Polymer Sci.: Part A: Polymer Chem., vol. 47, pp. 5565-5576 (2009).

(Continued)

*Primary Examiner* — Yong L Chu
(74) *Attorney, Agent, or Firm* — Venable LLP

(57) ABSTRACT

A borated benzoxazine compound, which can be used in particular as monomer in the synthesis of polybenzoxazine, corresponds to the formula:

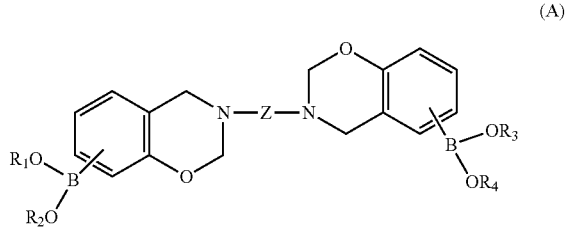

(A)

Figure 1A:
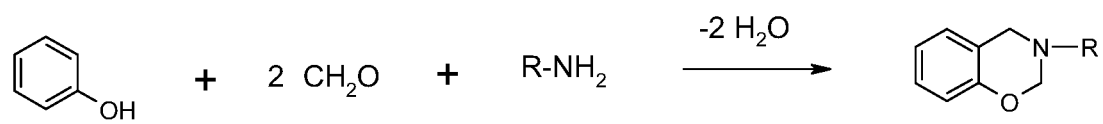

in which: Z represents an at least divalent, aliphatic, cycloaliphatic or aromatic, bonding group comprising at least one carbon atom and optionally at least one heteroatom chosen from O, S and P; and $R_1$, $R_2$, $R_3$ and $R_4$, which are identical or different, represent hydrogen or an alkyl comprising from 1 to 12 carbon atoms, it being possible for $R_1$ and $R_2$, on the one hand, and $R_3$ and $R_4$, on the other hand, optionally to form a heterocycle with the two oxygen atoms and the boron atom to which they are respectively bonded.

17 Claims, 24 Drawing Sheets

(56) References Cited

OTHER PUBLICATIONS

Co-pending U.S. Appl. No. 16/062,990, filed Dec. 5, 2016.
Co-pending U.S. Appl. No. 16/345,304, filed Sep. 25, 2017.
Co-pending U.S. Appl. No. 16/621,497, filed Jun. 12, 2018.
Co-pending U.S. Appl. No. 16/621,570, filed Jun. 12, 2018.

* cited by examiner

Monomer Mo

Monomer Mo

Δ | Borylation

Monomer M

(Ao-1)

Monomer Mo-1

Monomer Mo-2

Monomer Mo-3

Monomer Mo-4

Monomer Mo-5

Monomer Mo-1

Δ | Borylation

Monomer M-1

(Ao-4)

Monomer Mo-4

Δ | Borylation (A-4)

Monomer M-4

2     Compound 1     +     Compound 5     +     Compound 3

(Ao-7)

Monomer Mo-7

BORATED BENZOXAZINE FOR USE IN THE SYNTHESIS OF POLYBENZOXAZINE

1. FIELD OF THE INVENTION

The present invention relates to monomers which can be used in the synthesis of thermosetting resins, intended in particular for adhesive systems which make possible in particular the adhesive bonding of metal to rubber.

It more particularly relates to benzoxazine compounds suitable for the synthesis of polybenzoxazines which can be used in particular as adhesive layers in metal/rubber composites intended for the manufacture of rubber articles, such as pneumatic or non-pneumatic tyres, for vehicles.

2. STATE OF THE ART

Metal/rubber composites, in particular for vehicle tyres, are well known. They are most often composed of a matrix made of rubber, generally diene rubber, which can be crosslinked with sulfur, comprising metal reinforcing elements (or "reinforcers"), such as threads, films or cords made of carbon steel.

As they are subjected to very high stresses during the rolling of the tyres, in particular to repeated actions of compression, bending or variation in curvature, these composites must, in a known way, satisfy a large number of sometimes contradictory technical criteria, such as uniformity, flexibility, flexural strength and compressive strength, tensile strength, wear resistance and corrosion resistance, and must maintain these performance qualities at a very high level for as long as possible.

It is easily understood that the adhesive interphase between rubber and reinforcers plays a dominating role in the endurance of these performance qualities. The conventional process for connecting the rubber compositions to carbon steel consists in coating the surface of the steel with brass (copper/zinc alloy), the bonding between the steel and the rubber matrix being provided by sulfurization of the brass during the vulcanization or curing of the rubber. In order to improve the adhesion, use is generally made, in addition, in these rubber compositions, of organic salts or metal complexes, such as cobalt salts, as adhesion-promoting additives.

In point of fact, it is known that the adhesion between the carbon steel and the rubber matrix is liable to weaken over time as a result of the gradual development of the sulfides formed, under the effect of the various stresses encountered, in particular mechanical and/or thermal stresses, it being possible for the above degradation process to be accelerated in the presence of moisture. Moreover, the use of cobalt salts renders the rubber compositions more sensitive to oxidation and to ageing, and significantly increases the cost thereof, not to mention that it is desirable to eliminate, in the long run, the use of such cobalt salts in rubber compositions due to recent developments in European regulations relating to metal salts of this type.

For all the reasons set out above, manufacturers of metal/rubber composites, in particular vehicle tyre manufacturers, are seeking novel adhesive solutions in order to adhesively bond the metal reinforcers to the rubber compositions, while overcoming, at least in part, the abovementioned disadvantages.

Thus it is that the recently published applications WO 2014/063963, WO 2014/063968, WO 2014/173838 and WO 2014/173839, filed by the Applicant Companies, have described novel polymers comprising urea, urethane or thiourea units, and also their starting monomers, which meet the above objectives. Used in particular as adhesion primer on metal in metal/rubber composites, these polymers make it possible very advantageously to adhesively bond the metal to the rubber matrices by subsequently using simple textile adhesives, such as "RFL" (resorcinol/formaldehyde latex) adhesives or other equivalent adhesive compositions, or else directly (that is to say, without employing such adhesives) to these rubber matrices when the latter contain, for example, appropriate functionalized unsaturated elastomers, such as epoxidized elastomers. Thus, the cobalt salts (or other metal salts) can in particular be dispensed with in the rubber compositions intended to be connected to brass-coated metal reinforcers.

On continuing their research studies, the Applicant Companies have found a novel benzoxazine compound, which can be used as monomer in the synthesis of a polybenzoxazine, of the thermosetting type, which, at ambient temperature, exhibits the same adhesive performance qualities, with regard to the metal and the rubber, as the abovementioned polymers but which exhibits, once thermoset (crosslinked), a thermal and chemical stability which is even improved and the specific microstructure of which additionally makes it possible very advantageously to adjust the flexibility of the molecule according to the particular applications targeted.

3. SUMMARY OF THE INVENTION

The present invention relates to a borated benzoxazine corresponding to the formula (A) below:

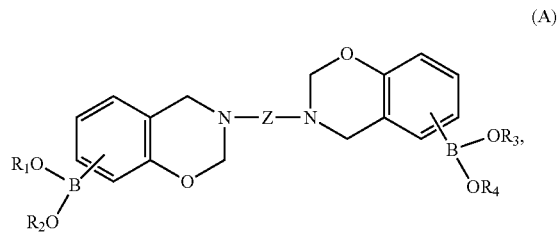

(A)

in which:
  Z represents an at least divalent, aliphatic, cycloaliphatic or aromatic, bonding group comprising at least one carbon atom and optionally at least one heteroatom chosen from O, S and P;
  $R_1$, $R_2$, $R_3$ and $R_4$, which are identical or different, represent hydrogen or an alkyl comprising from 1 to 12 carbon atoms, it being possible for $R_1$ and $R_2$, on the one hand, $R_3$ and $R_4$, on the other hand, optionally to form a heterocycle with the two oxygen atoms and the boron atom to which they are respectively bonded.

By virtue of this specific benzoxazine, it is possible to prepare benzoxazine polymers or "polybenzoxazines" which have the remarkable ability, at high temperature, to open their oxazine rings and to thus result in a thermosetting polyphenol resin structure. This confers on them, in comparison with the other known polymers described in the introduction to the present document, a better thermal stability. Finally, its specific microstructure makes it possible very advantageously to adjust the flexibility of the polybenzoxazines depending on the particular applications targeted.

The invention also relates to the use of a compound in accordance with the invention in the synthesis of a polybenzoxazine.

The invention also relates to any process for the synthesis of a polybenzoxazine by polycondensation of a borated benzoxazine according to the invention (as first monomer), in particular with (as second monomer) a brominated benzoxazine corresponding to the formula (B) below:

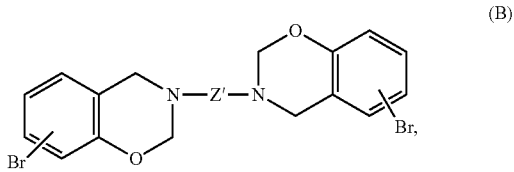

(B)

in which formula (B) Z', which is identical to or different from Z defined above, itself represents an at least divalent, aliphatic, cycloaliphatic or aromatic, bonding group comprising at least one carbon atom and optionally at least one heteroatom chosen from O, S and P.

4. BRIEF DESCRIPTION OF THE FIGURES

Figure 1B:
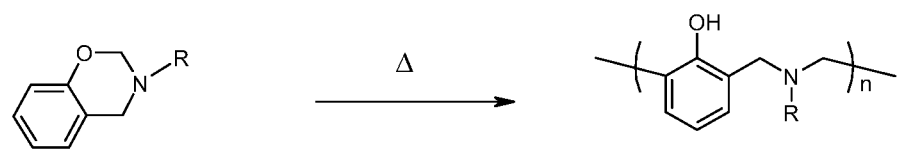
Figure 2:
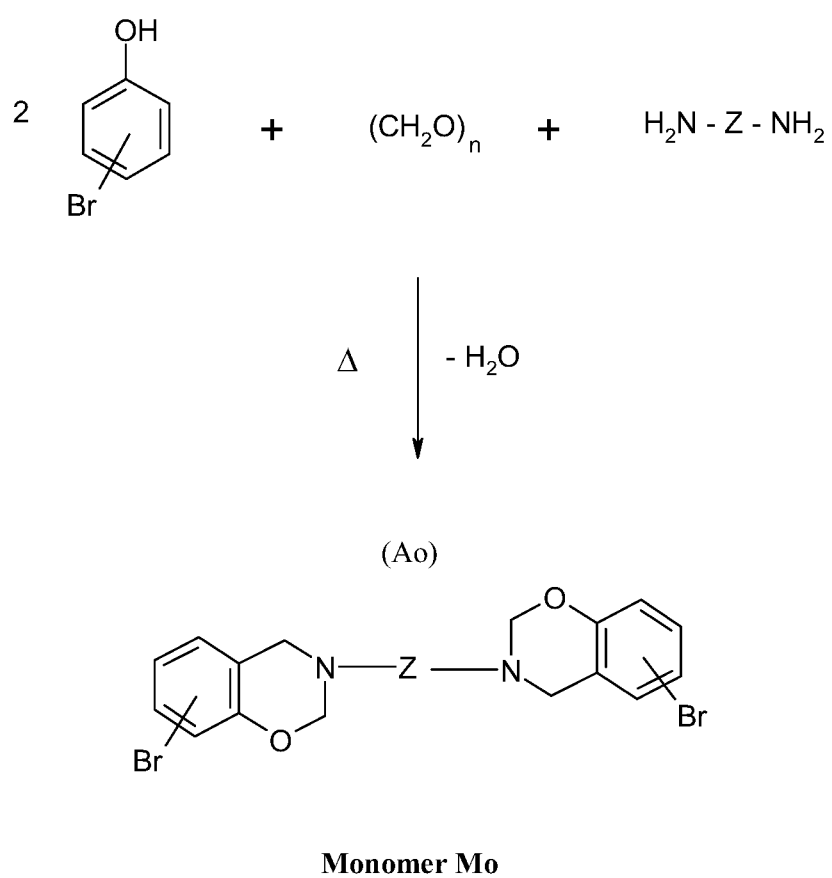
Figure 3:
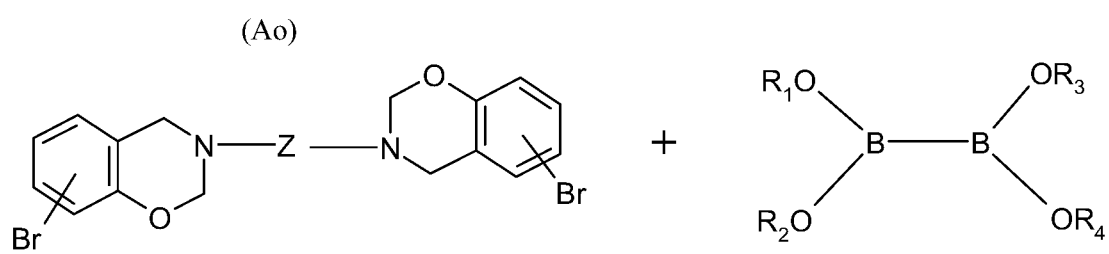
Figure 3:
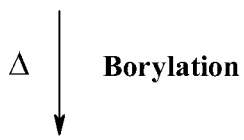
Figure 3:
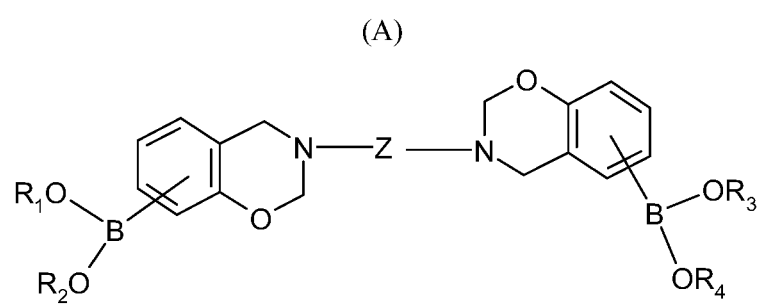
Figure 4:
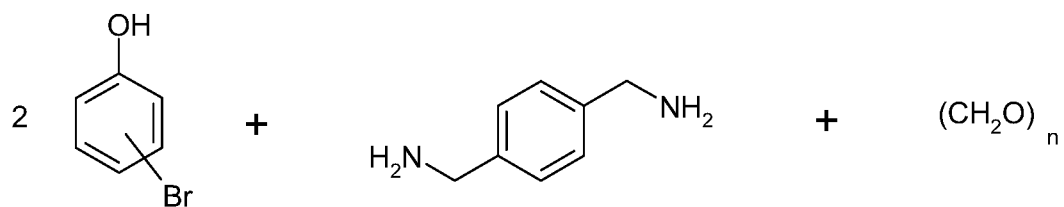
Figure 4:
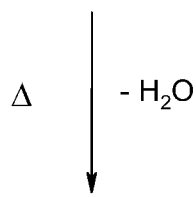
Figure 4:
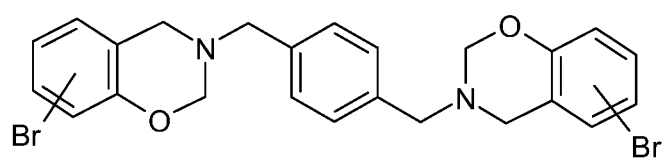
Figure 5:
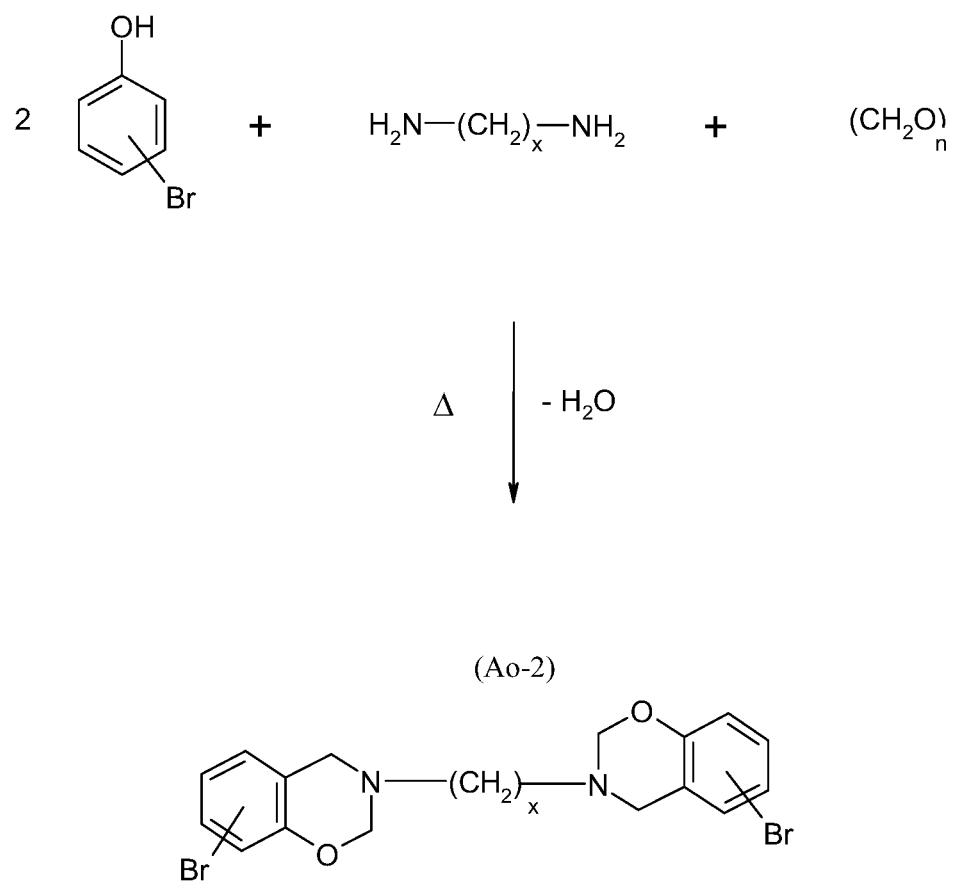
Figure 6:
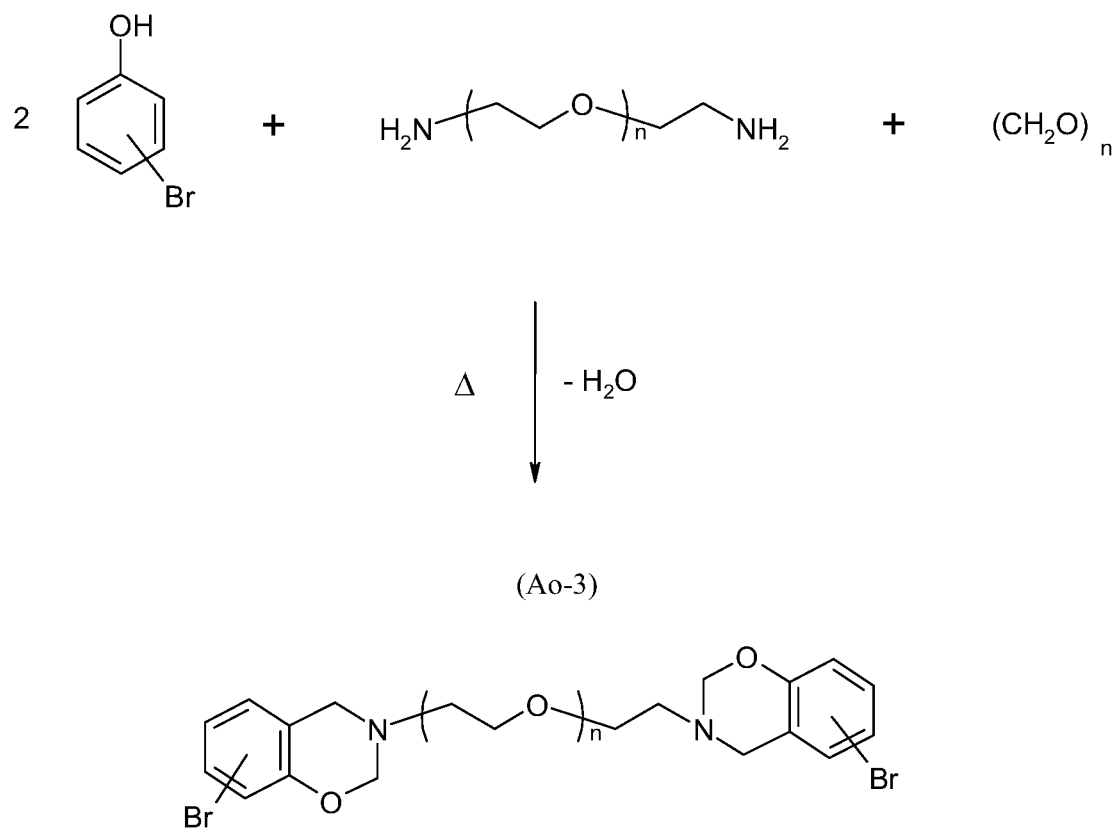
Figure 7:
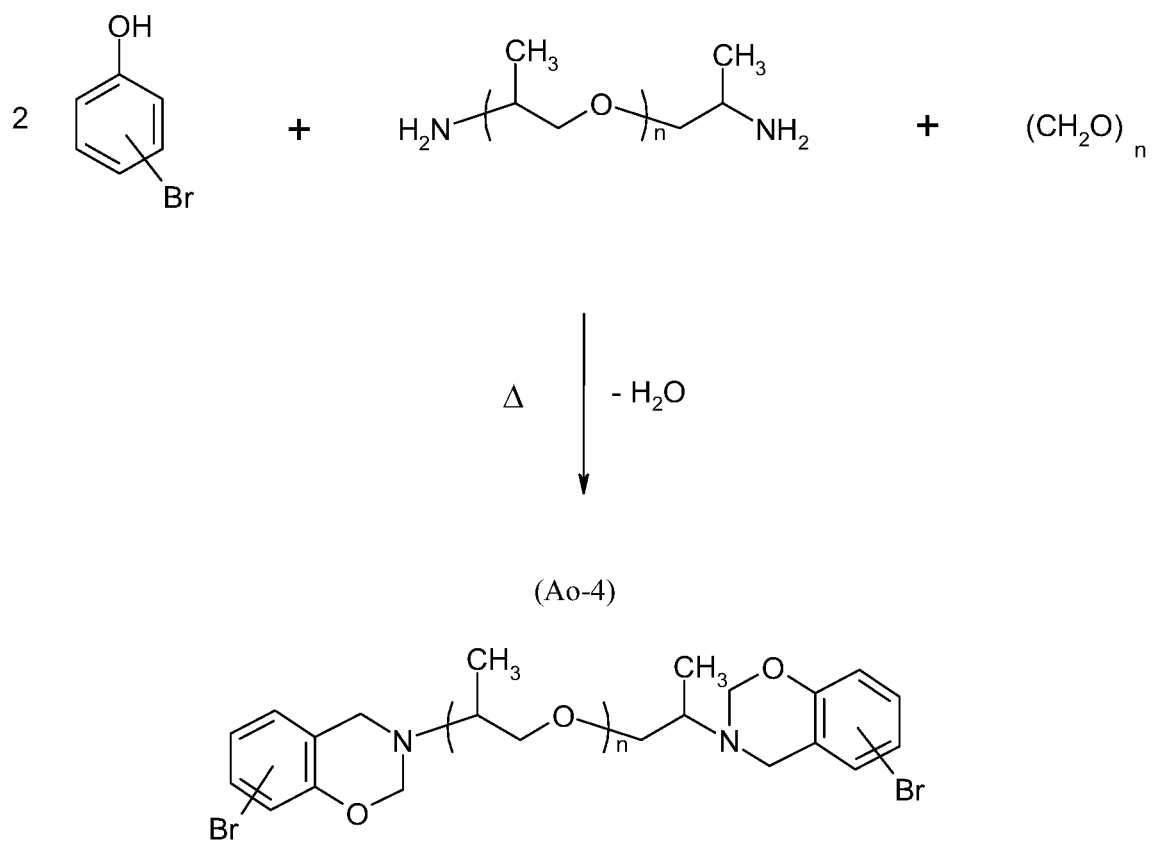
Figure 8:
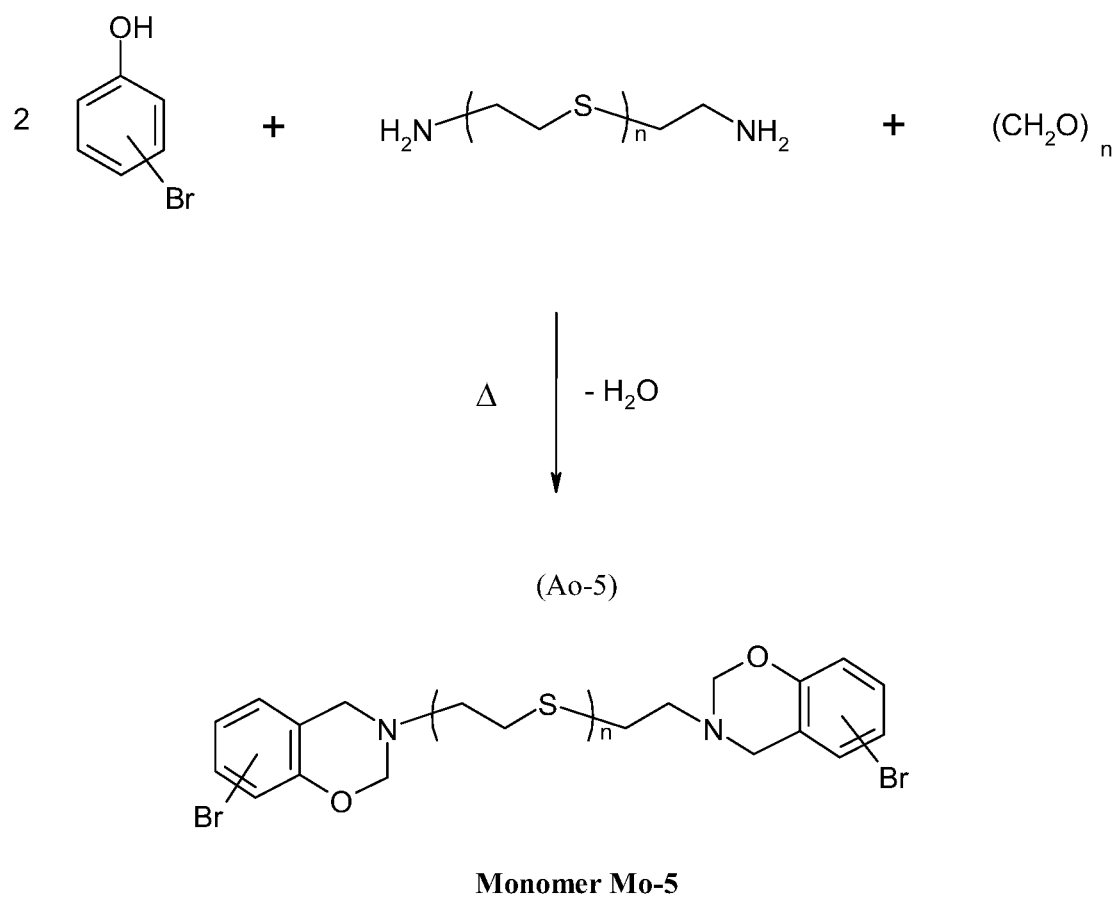
Figure 9:
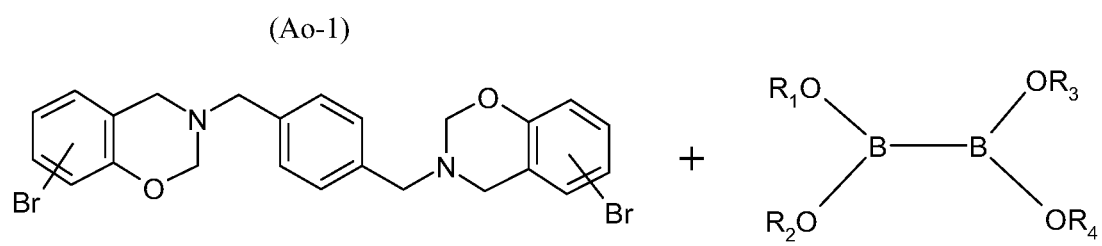
Figure 9:
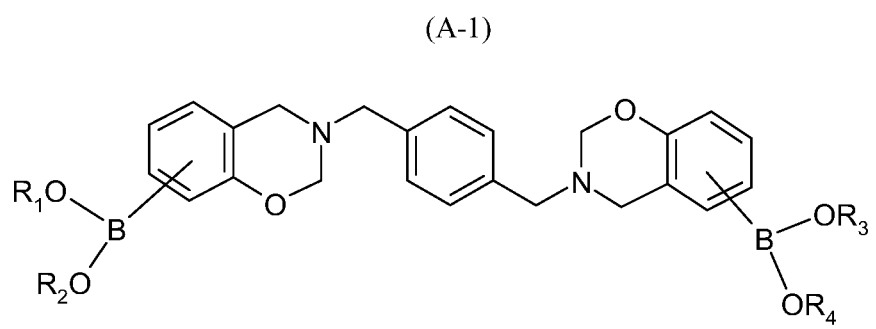
Figure 10:
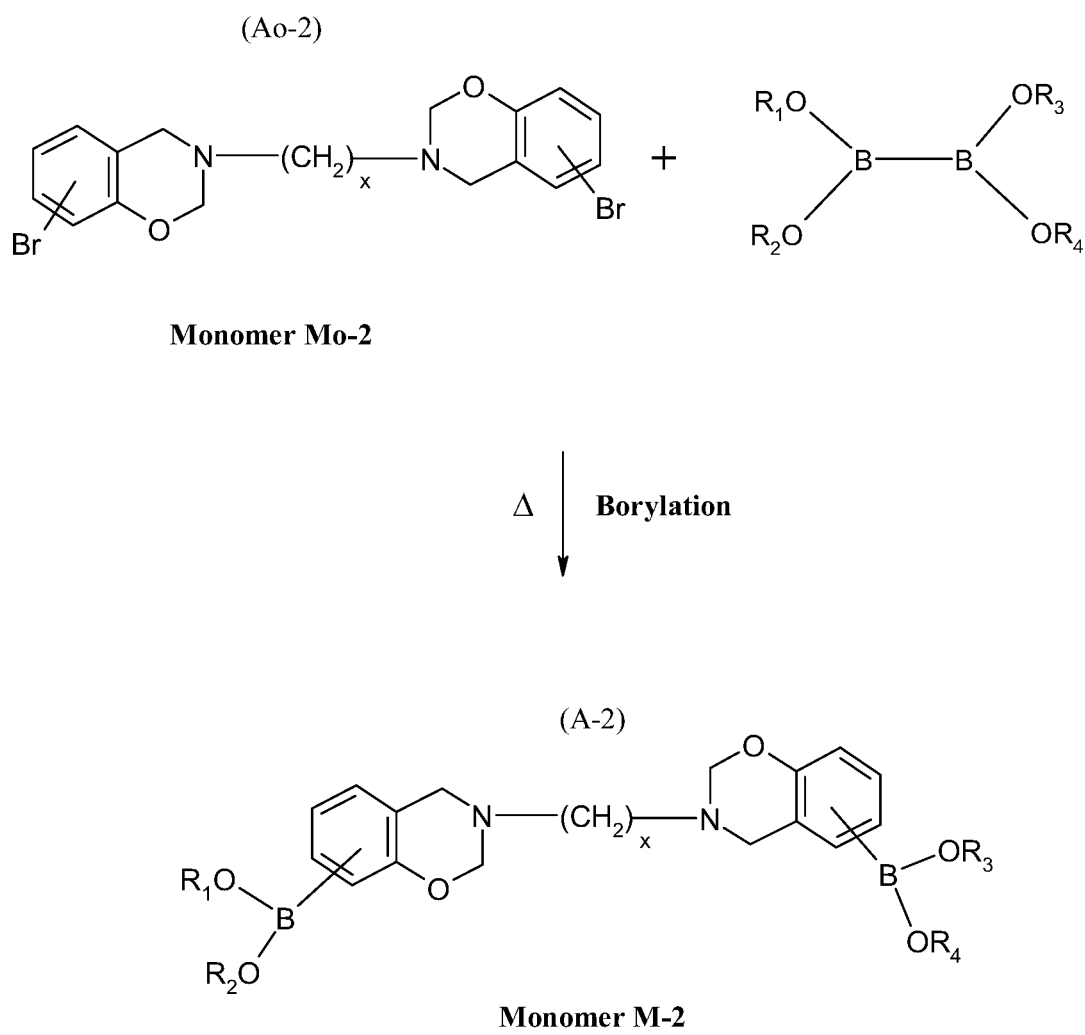
Figure 11:
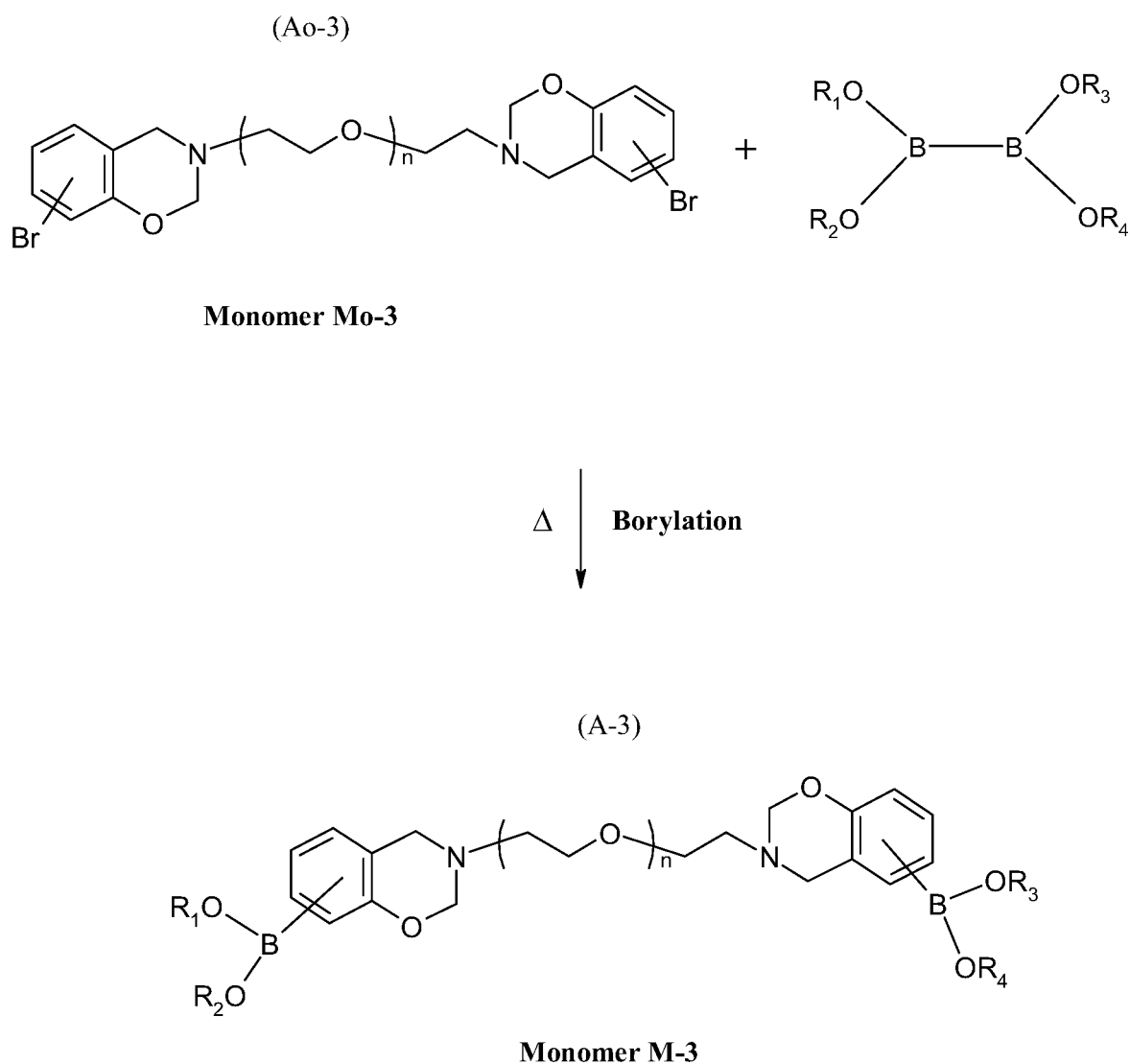
Figure 12:
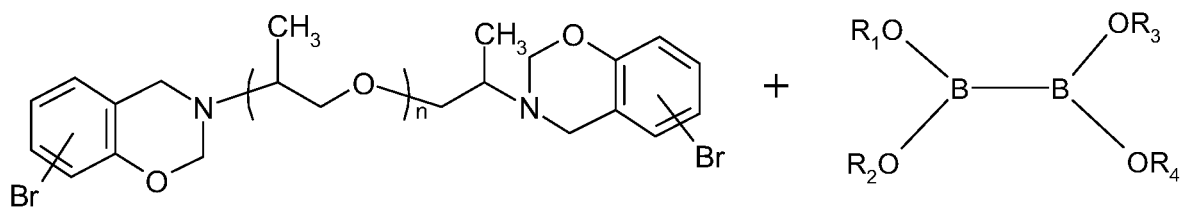
Figure 12:
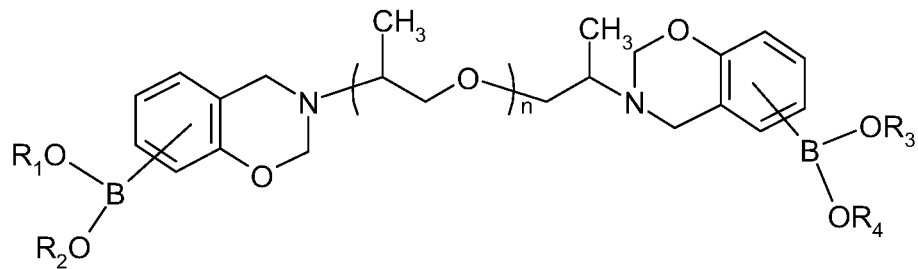
Figure 13:
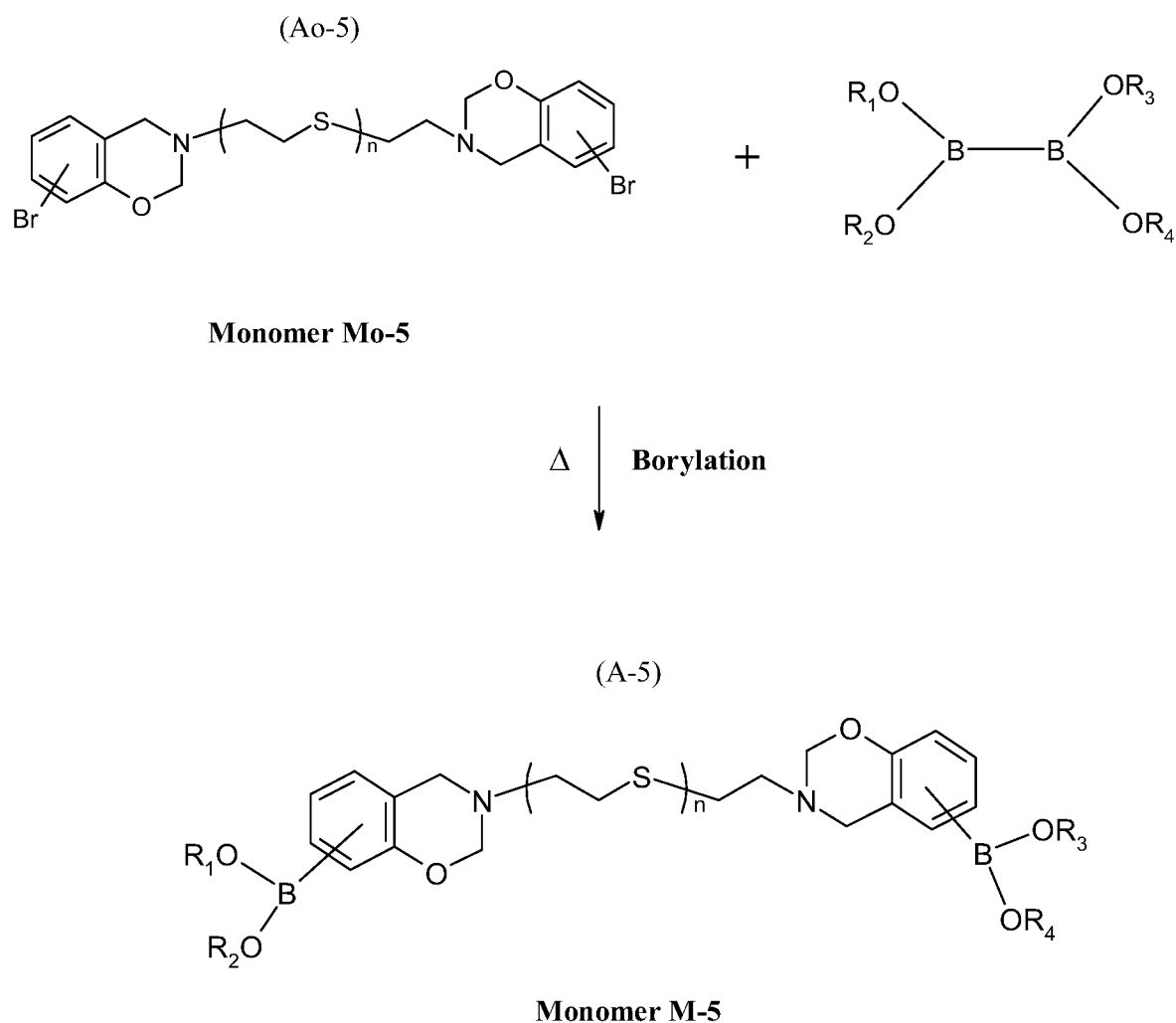
Figure 14:
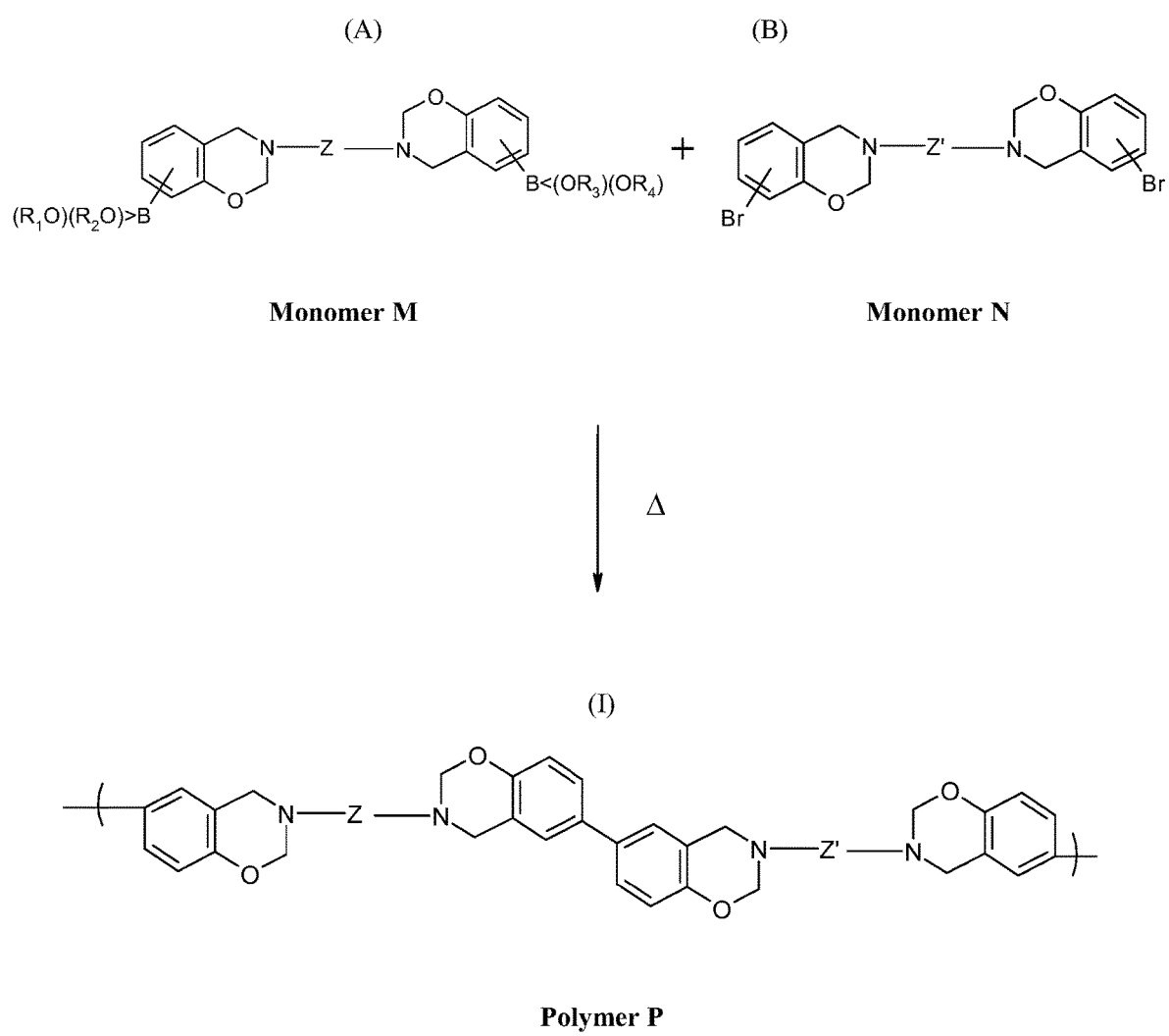
Figure 15:
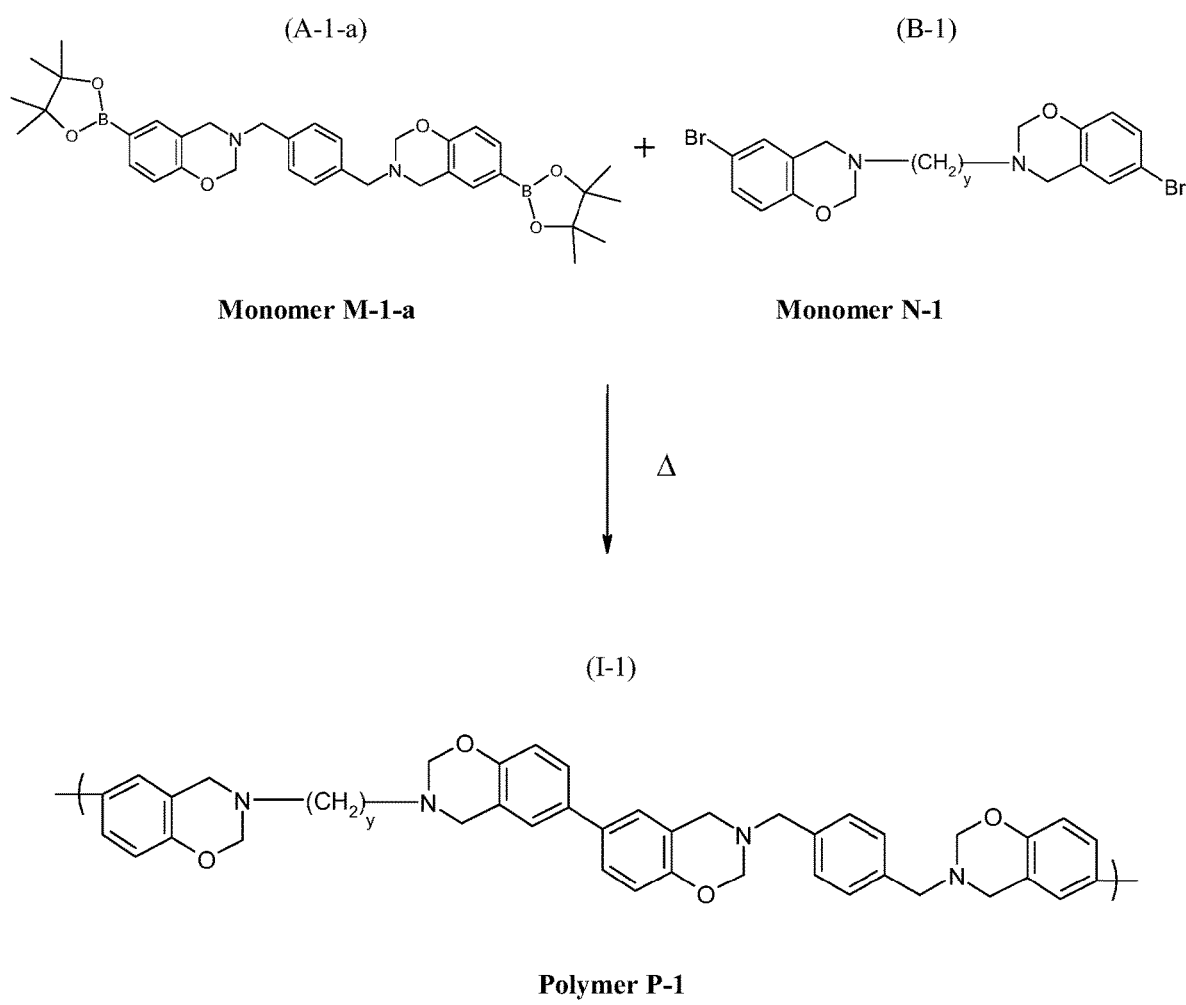
Figure 16:
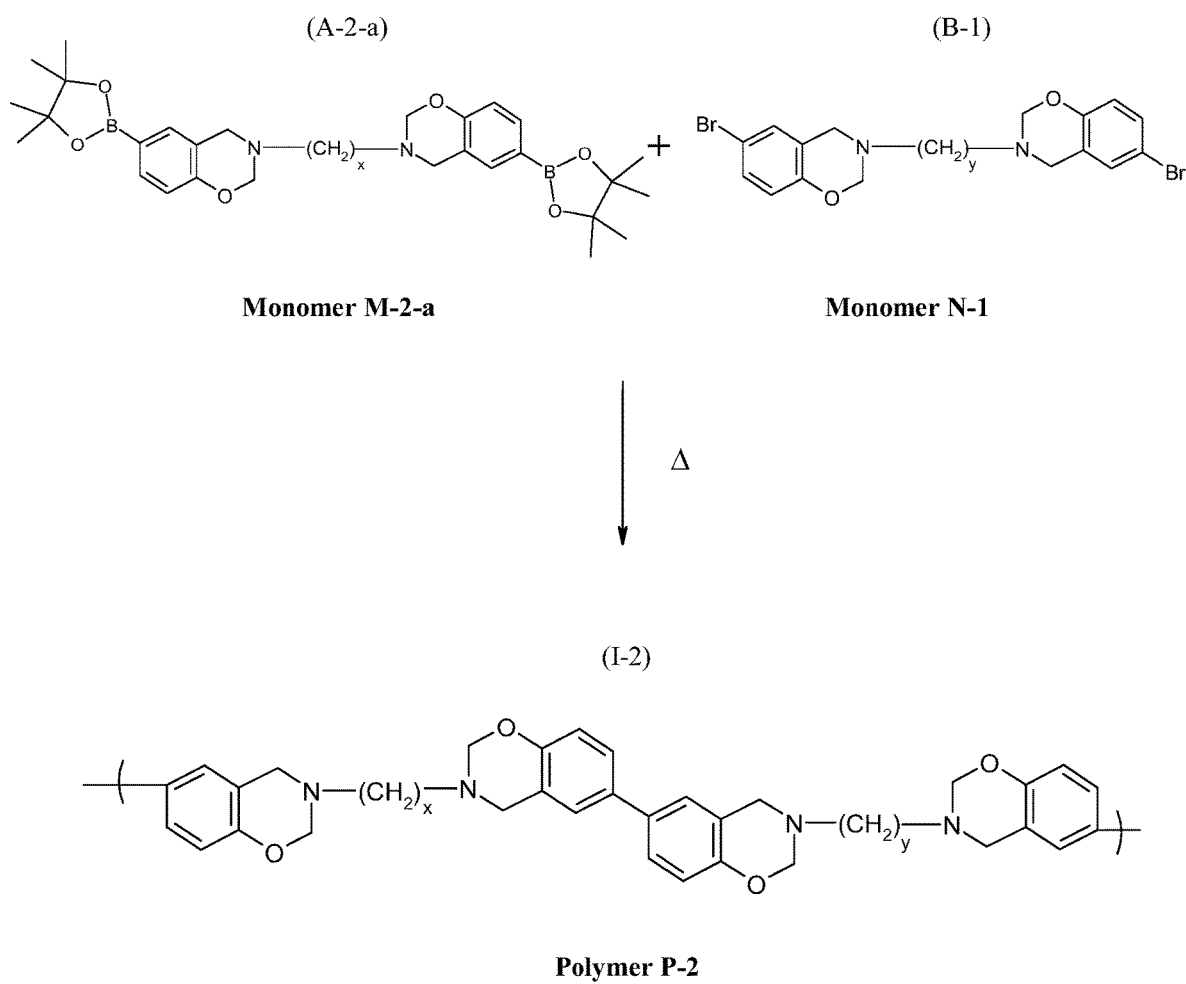
Figure 17:
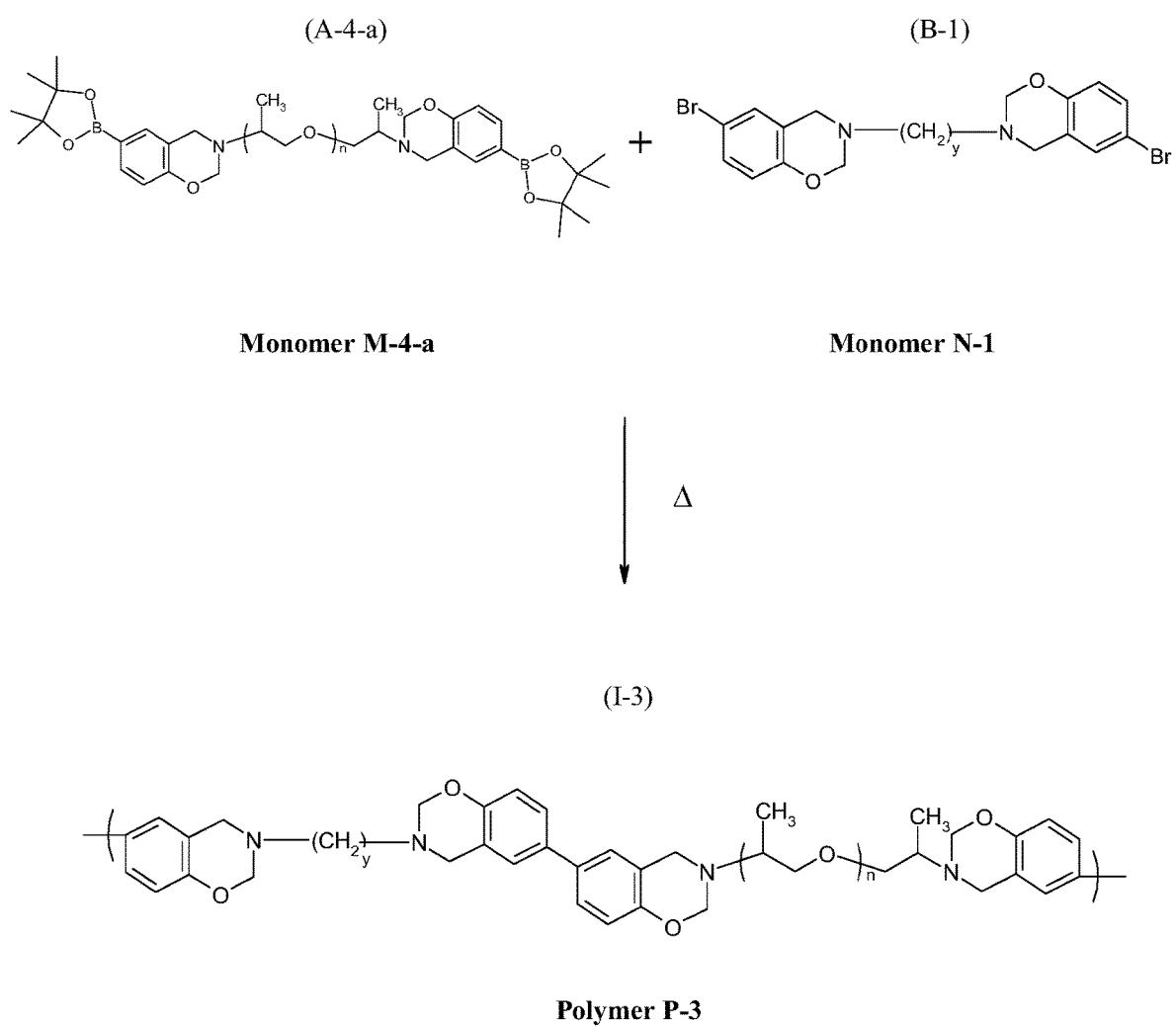
Figure 18:
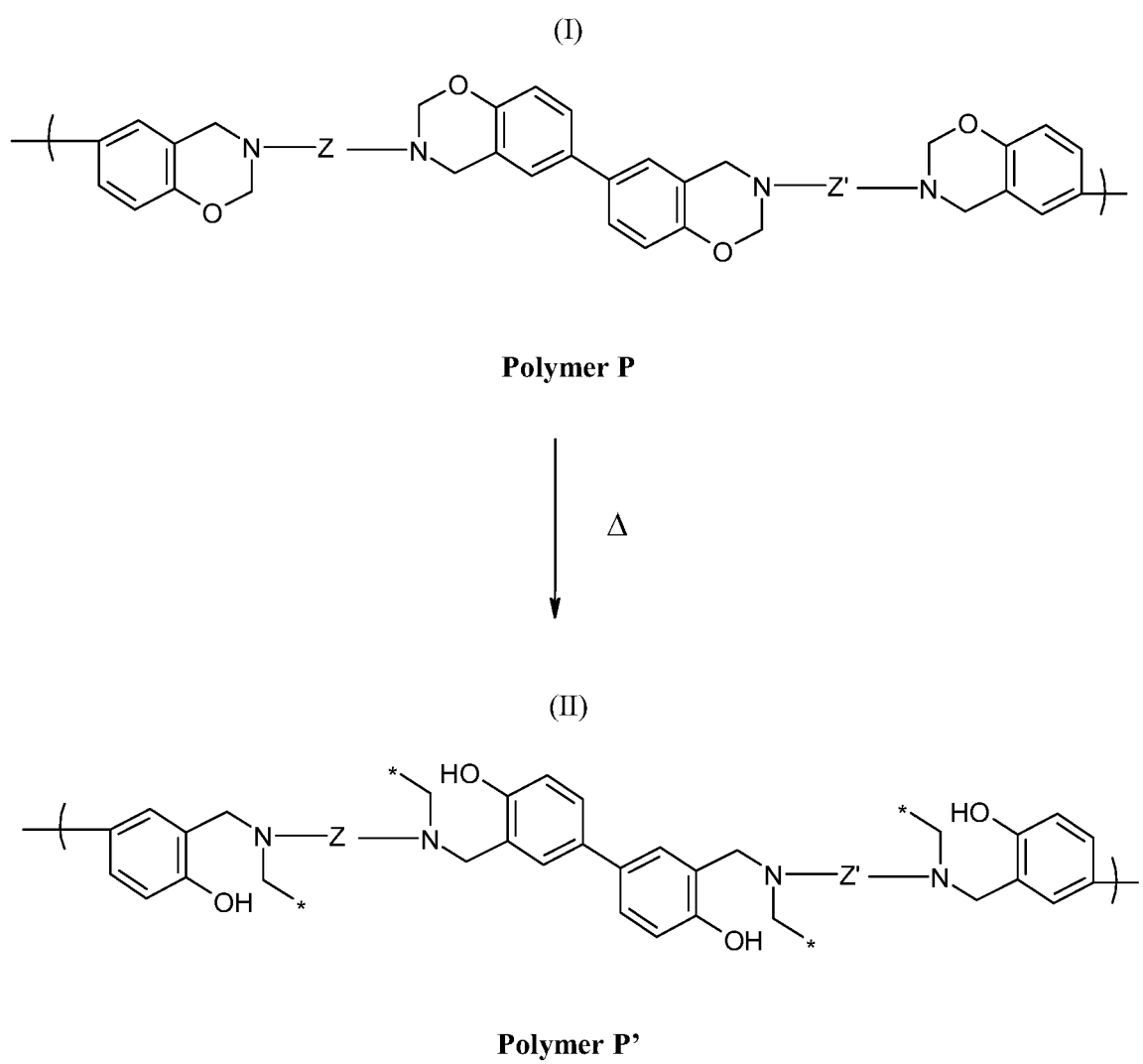
Figure 19:
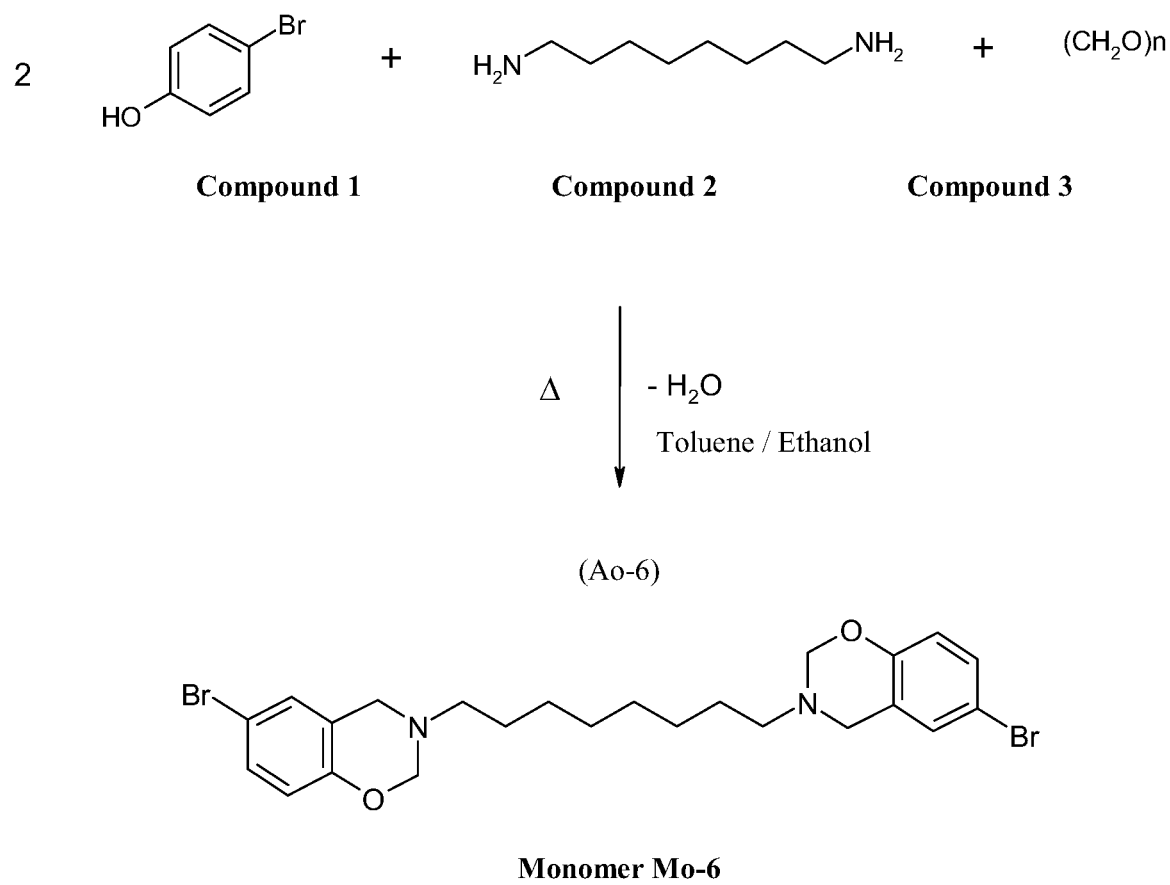
Figure 20:
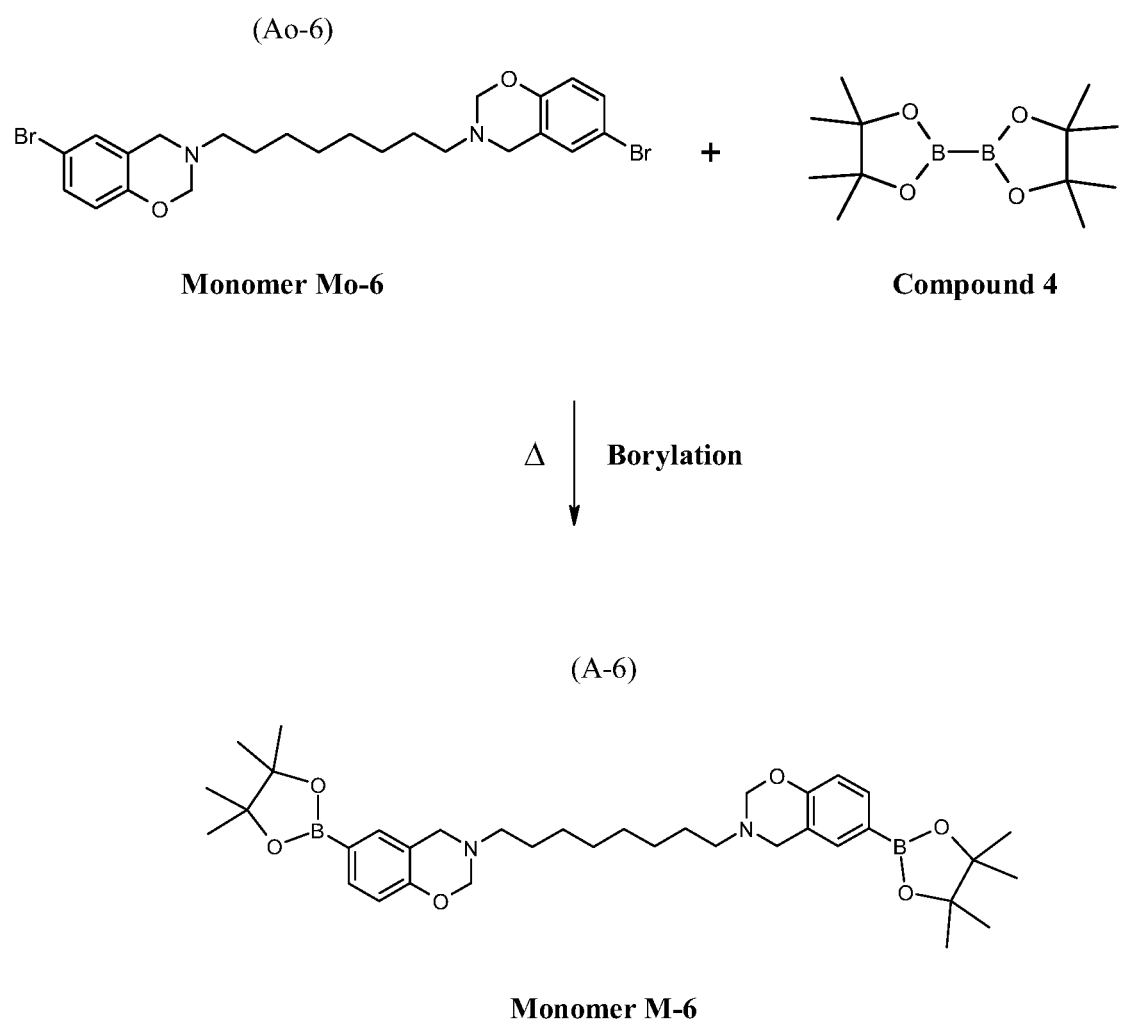
Figure 21:
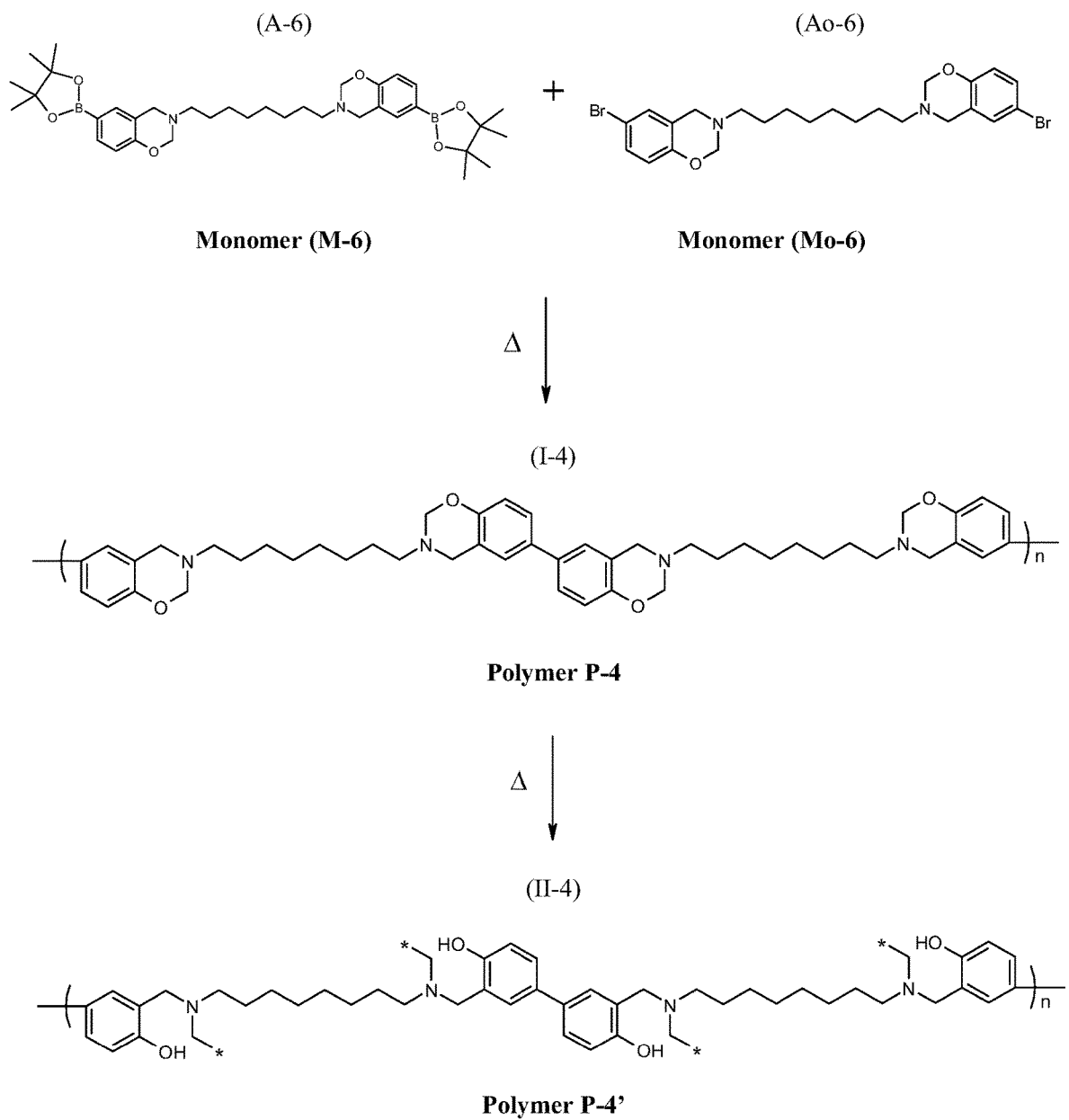
Figure 22:
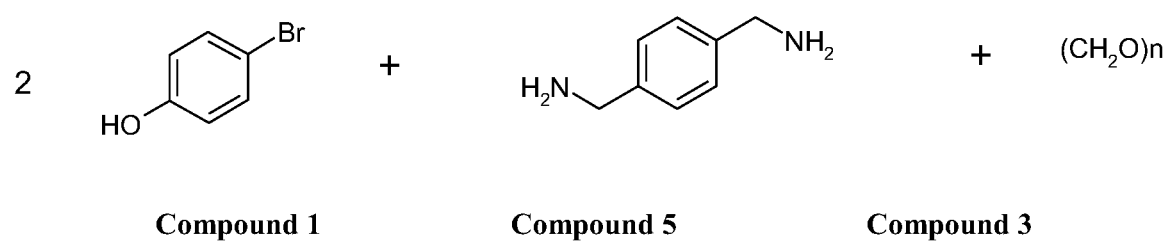
Figure 22:
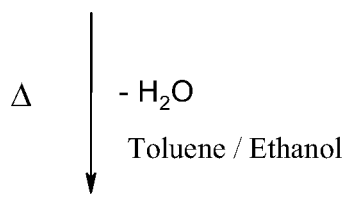
Figure 22:
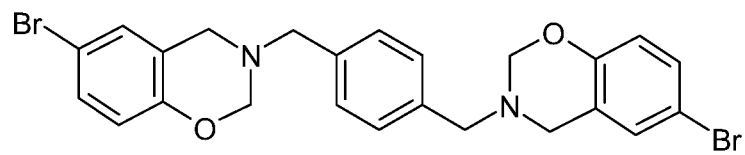
Figure 23:
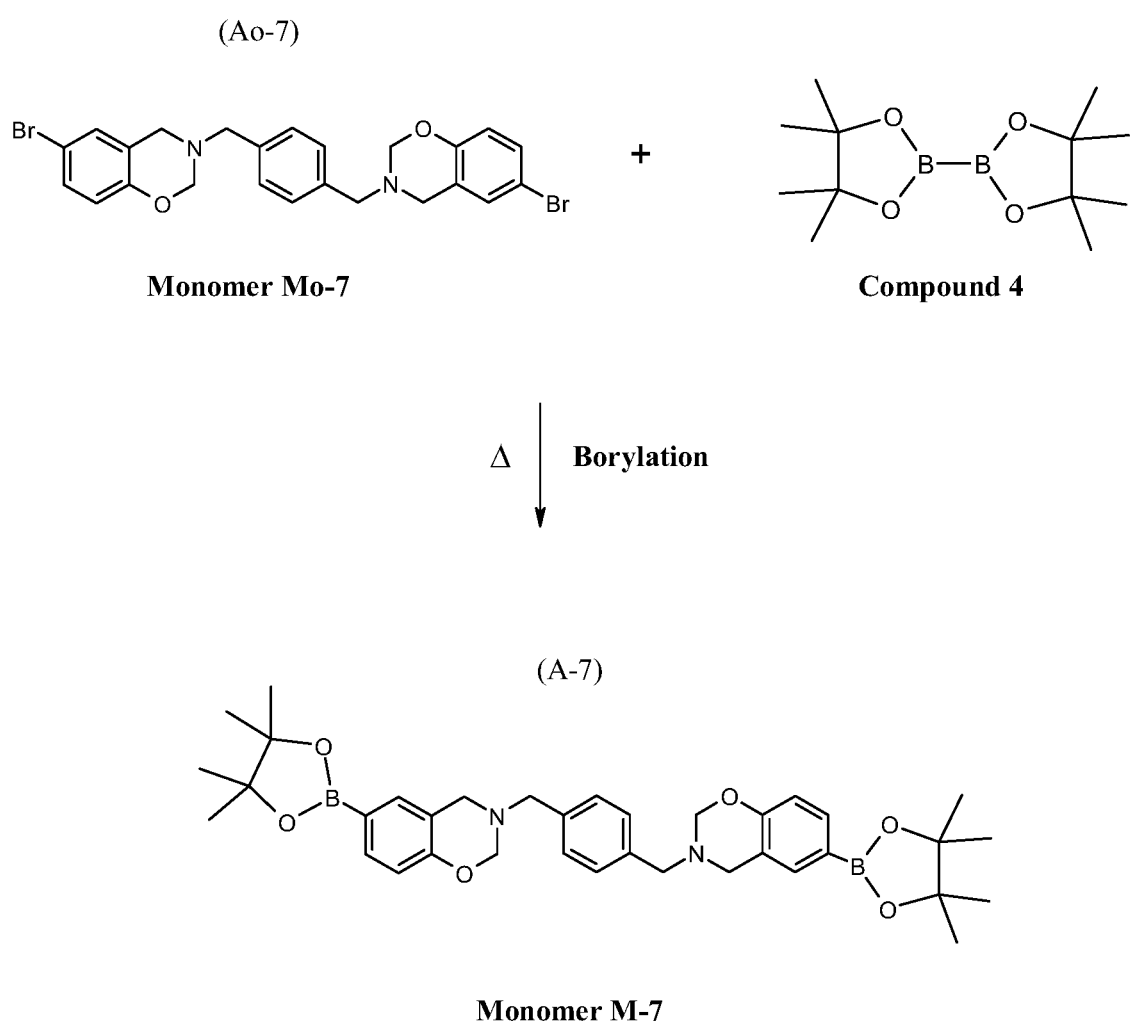
Figure 24:
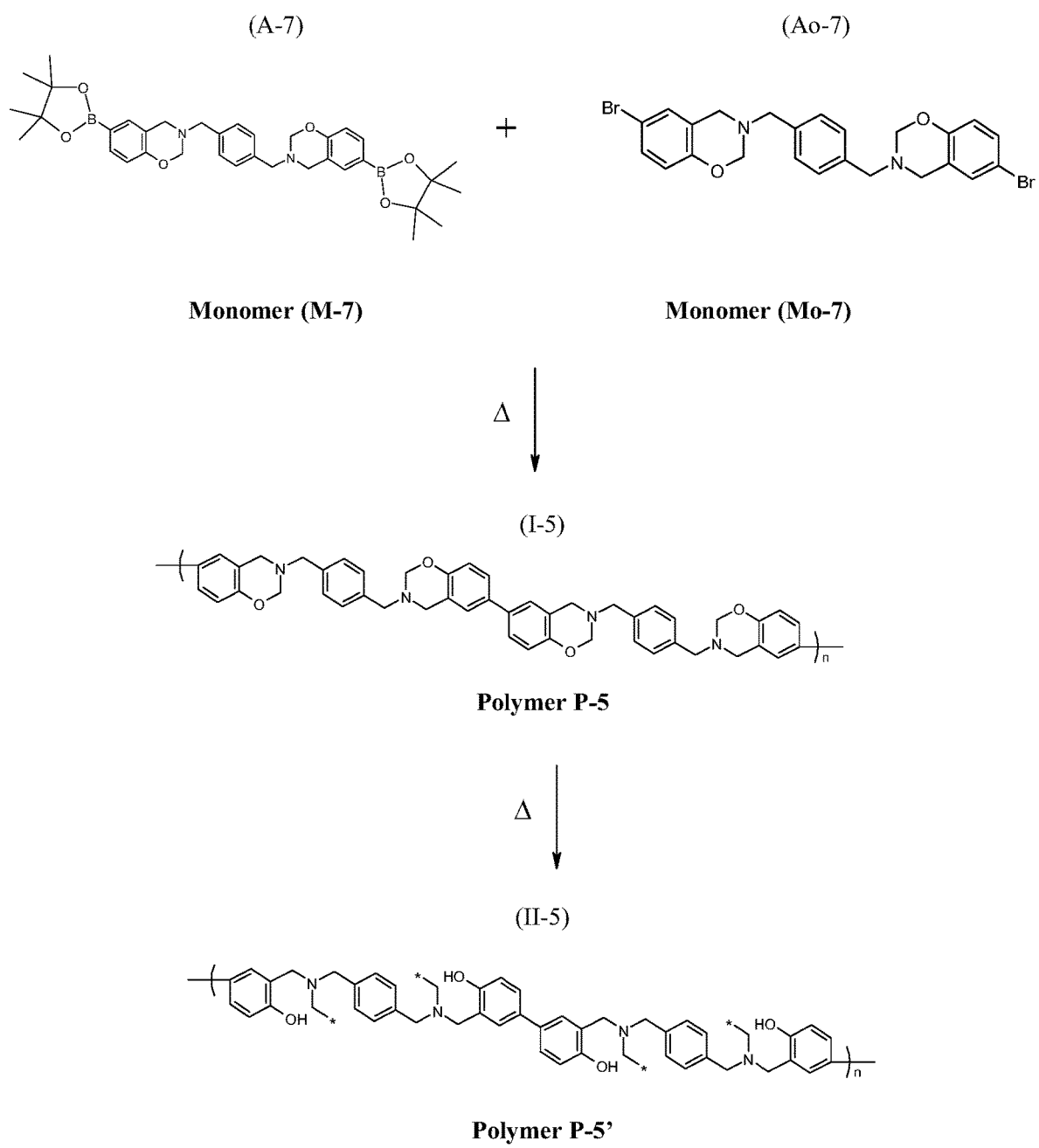

The invention and its advantages will be easily understood in the light of the detailed description and of the implementational examples which follow, and also of FIGS. 1 to 24 relating to these examples, which represent or diagrammatically represent:

the general principle for the synthesis of a benzoxazine compound starting from three compounds, phenol, formaldehyde and amine (R=residue of the amine) (FIG. 1a);

the mechanism for opening, by heat input, the oxazine ring (ring-opening) of such a benzoxazine compound (FIG. 1b);

a scheme for the synthesis, starting from a brominated phenol (Br representing a bromine atom), paraformaldehyde and a diamine, of a brominated benzoxazine of formula (Ao), which can be used as starting compound (Monomer denoted "Mo") in the synthesis of a borated benzoxazine according to the invention (FIG. 2);

a general scheme for the synthesis of a borated benzoxazine of formula (A), in accordance with the invention, by a reaction for the borylation of a brominated benzoxazine of preceding formula (Ao) by a diboronic (ester or acid) compound, this borated benzoxazine being able to be used as starting monomer (Monomer denoted "M") in the synthesis of a polybenzoxazine (FIG. 3);

a possible scheme for the synthesis, starting from a brominated phenol, paraformaldehyde and a specific diamine of the aromatic type, of a particular brominated benzoxazine of formula (Ao-1) which can be used as starting compound (Monomer denoted Mo-1) in the synthesis of a particular borated benzoxazine in accordance with the invention (FIG. 4);

another possible scheme for the synthesis, starting from a halogenated phenol, paraformaldehyde and another specific diamine, this time of the aliphatic type, of another example of particular brominated benzoxazine of formula (Ao-2) which can be used as starting monomer (Monomer denoted Mo-2) in the synthesis of another example of borated benzoxazine in accordance with the invention (FIG. 5);

three other possible schemes for the synthesis, starting from a halogenated phenol, paraformaldehyde and specific diamines, which are all aliphatic, of other examples of particular brominated benzoxazines, of respective formulae (Ao-3), (Ao-4) and (Ao-5), which can all be used as starting monomer (Monomers denoted Mo-3, Mo-4 and Mo-5 respectively) in the synthesis of other examples of borated benzoxazines according to the invention (FIG. 6, FIG. 7 and FIG. 8);

a scheme for the synthesis of an example of borated benzoxazine in accordance with the invention, of formula (A-1), by borylation of the brominated benzoxazine of preceding formula (Ao-1) using a diboronic ester or acid, this borated benzoxazine according to the invention being able to be used as starting monomer (Monomer denoted M-1) in the synthesis of a polybenzoxazine (FIG. 9);

various other schemes for the synthesis of other examples of borated benzoxazines in accordance with the invention, of respective formulae (A-2), (A-3), (A-4) and (A-5), by borylation of the brominated benzoxazines of preceding respective formulae (Ao-2), (Ao-3), (Ao-4) and (Ao-5), using a diboronic ester or acid, these borated benzoxazines according to the invention being able to be used as starting monomers (Monomers denoted M-2, M-3, M-4 and M-5 respectively) in the synthesis of polybenzoxazines (FIG. 10, FIG. 11, FIG. 12 and FIG. 13);

a general scheme for the synthesis of a polybenzoxazine polymer (Polymer denoted "P") by polycondensation of the borated benzoxazine of the invention of formula (A) (Monomer M) of preceding FIG. 3 and of another benzoxazine of generic formula (B) (Monomer denoted "N") of the brominated type (FIG. 14);

a particular scheme for the synthesis of a particular polybenzoxazine polymer (Polymer denoted P-1), starting from a specific borated benzoxazine according to the invention of formula (A-1-a) (Monomer M-1-a) and another benzoxazine of generic formula (B-1) (Monomer denoted N-1) of the brominated type (FIG. 15);

two other possible schemes for the synthesis of particular polybenzoxazine polymers (Polymers denoted P-2 and P-3 respectively) by polycondensation of specific borated benzoxazines according to the invention of respective formulae (A-2-a) and (A-4-a) (Monomers M-2-a and M-4-a) with the other benzoxazine of generic formula (B-1) (Monomer N-1) of the brominated type (FIG. 16 and FIG. 17);

the polybenzoxazine (Polymer denoted "P'" in this instance) of FIG. 14 once its oxazine rings have been opened after heat treatment of the Polymer P (FIG. 18);

the scheme for the synthesis, starting from a brominated phenol (compound 1), paraformaldehyde (compound 3) and a specific aliphatic diamine (compound 2), of a particular brominated dibenzoxazine of formula (Ao-6) (Monomer denoted Mo-6) which can be used in the synthesis of a borated benzoxazine in accordance with the invention (FIG. 19);

a specific scheme for the synthesis of a borated benzoxazine according to the invention, of formula (A-6), by borylation of the brominated benzoxazine of preceding formula (Ao-6) using a diboronic ester (bispinacol ester of boric acid) (compound 4), this borated benzoxazine according to the invention being able to be used as starting monomer (Monomer denoted M-6) in the synthesis of a polybenzoxazine (FIG. 20);

a specific scheme for the synthesis of an example of particular polybenzoxazine polymer (Polymer denoted P-4) by polycondensation of the preceding specific borated benzoxazine according to the invention of formula (A-6) (Monomer M-6) with its equivalent starting benzoxazine of formula (Ao-6) (Monomer Mo-6) of the brominated type, and also this same polybenzoxazine (Polymer denoted P-4') once its oxazine rings have been opened after heat treatment of the Polymer P-4 (FIG. 21);

another scheme for the synthesis, starting from a brominated phenol (compound 1), paraformaldehyde (compound 3) and another specific diamine, in this instance of aromatic type (compound 5), of a particular brominated dibenzoxazine of formula (Ao-7) (Monomer denoted Mo-7) which can be used in the synthesis of a borated benzoxazine in accordance with the invention (FIG. 22);

a specific scheme for the synthesis of a borated benzoxazine in accordance with the invention, of formula (A-7), by borylation of the brominated benzoxazine of preceding formula (Ao-7) using a diboronic ester (bispinacol ester of boric acid) (compound 4), this borated benzoxazine according to the invention being able to be used as starting monomer (Monomer denoted M-7) in the synthesis of a polybenzoxazine (FIG. 23);

finally, a specific scheme for the synthesis of an example of particular polybenzoxazine polymer (Polymer denoted P-5) by polycondensation of the preceding specific borated benzoxazine according to the invention of formula (A-7) (Monomer M-7) with its equivalent starting benzoxazine of formula (Ao-7) (Monomer Mo-7) of the brominated type, and also this same polybenzoxazine (Polymer denoted P-5') once its oxazine rings have been opened after heat treatment of the Polymer P-5 (FIG. 24).

5. DETAILED DESCRIPTION OF THE INVENTION

It will first of all be recalled that benzoxazines are compounds of general formula:

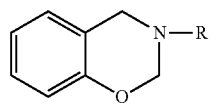

The appended FIG. 1a recalls the general principle of the synthesis of a benzoxazine, in this instance starting (condensation reaction) from one molecule of phenol, from two molecules of formaldehyde and from an amine (R denoting the residue of the amine), with elimination of two molecules of water.

FIG. 1b for its part recalls the mechanism for opening the oxazine ring (ring-opening) of such a compound during a heat input (represented by the symbol Δ).

Numerous benzoxazine compounds or monomers can thus be synthesized using various phenols and amines according to their types of substituents. These substituting groups may subsequently provide polymerizable sites and make possible the synthesis of various benzoxazine polymers (or polybenzoxazines).

Benzoxazines and polybenzoxazines which result therefrom are products which are today well known to a person skilled in the art; to cite but a few publication examples, mention may be made of the papers "*Polybenzoxazines—New high performance thermosetting resins: synthesis and properties*"; N. N. Ghosh et al., Prog. Polym. Sci., 32 (2007), 1344-1391, or "*Recent Advancement on Polybenzoxazine—A Newly Developed High Performance Thermoset*", Y. Yaggi et al., J. Polym. Sci. Part A: Polym. Chem., Vol. 47 (2009), 5565-5576, and also, for example, of the patents or patent applications U.S. Pat. No. 5,543,516 and WO 2013/148408.

As explained in detail in the above documents, polybenzoxazines have the remarkable ability, at high temperature (for example, typically greater than 150° C., indeed even greater than 200° C., depending on their particular microstructure), to open their oxazine rings and to thus result in thermosetting polyphenol resin structures.

The specific benzoxazine of the invention, designated "Monomer M" in the present patent application, is of the borated type; it corresponds to the generic formula (A) which follows (the symbol B representing, of course, a Boron atom):

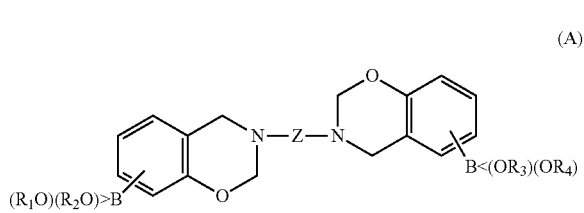

in which:
Z represents an at least divalent, aliphatic, cycloaliphatic or aromatic, bonding group comprising at least one carbon atom and optionally at least one heteroatom chosen from O, S and P;

$R_1$, $R_2$, $R_3$ and $R_4$, which are identical or different, represent hydrogen or an alkyl comprising from 1 to 12 carbon atoms.

In the formula (A) above, $R_1$ and $R_2$, on the one hand, $R_3$ and $R_4$, on the other hand, can optionally form a heterocycle with the two oxygen atoms and the boron atom to which they are respectively bonded; it will be easily understood that, in such a case, these alkyls are more specifically cycloalkyls.

The appended FIG. 3 gives the general scheme for the synthesis thereof by "borylation" reaction of a starting brominated benzoxazine of formula (Ao) with a diboronic compound (ester or acid), FIG. 2 for its part reproducing the process for the synthesis of this starting benzoxazine of formula (Ao), under heat input and with removal of water, starting from a halogenated phenol, paraformaldehyde and a diamine.

In the formula (A) above, Z represents a bonding group (spacer) which is at least divalent, that is to say that it might comprise more than two covalent bonds, for example three or four covalent bonds. Preferably, Z is divalent, that is to say comprises only two covalent bonds.

Z can be aliphatic, cycloaliphatic or aromatic. This Z group, which can be ethylenically saturated or unsaturated, by definition comprises at least one (that is to say, one or more) carbon atom, and optionally at least one (that is to say, one or more) heteroatom chosen from O (oxygen), S (sulfur) and P (phosphorus).

According to a preferred embodiment of the invention, Z comprises at least one aromatic group comprising from 6 to 30, preferably from 6 to 20, carbon atoms (and optionally at least one heteroatom chosen from O, S and P).

In such a case, the compound of the invention corresponds in particular to the formula (A-1) below:

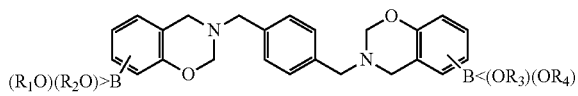

(A-1)

According to another preferred embodiment of the invention, Z represents an aliphatic group comprising from 1 to 20, preferably from 1 to 16, carbon atoms, or a cycloaliphatic group comprising from 3 to 20, preferably from 3 to 16, carbon atoms (and optionally at least one heteroatom chosen from O, S and P).

More preferably, Z represents a (poly)alkylene (or alkylidene) group or sequence comprising from 1 to 20, preferably from 1 to 16, carbon atoms (and optionally at least one heteroatom chosen from O, S and P). More preferably still, Z represents a (poly)alkylene sequence comprising from 1 to 12 carbon atoms and optionally at least one heteroatom chosen from O and S.

In such a case, the compound of the invention corresponds more preferably to one of the formulae (A-2) to (A-5) below:

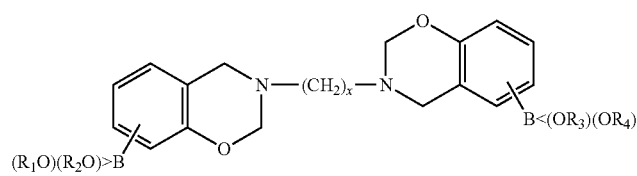

(A-2)

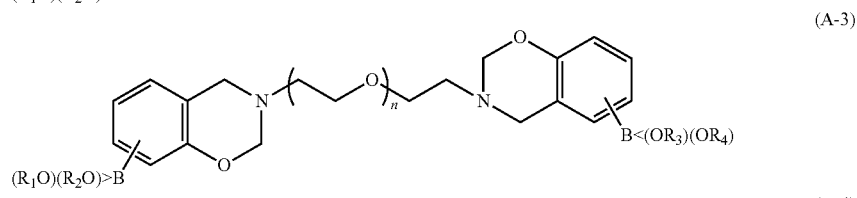

(A-3)

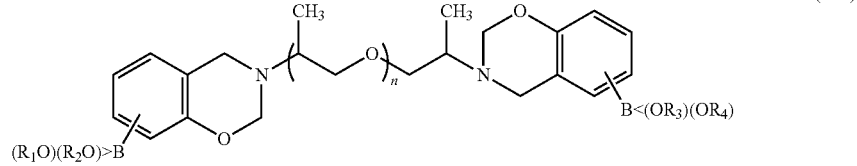

(A-4)

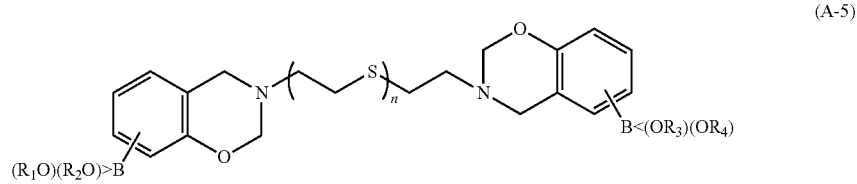

(A-5)

In the preceding formula (A) and in particular in the formulae (A-1) to (A-5) above, the symbols $R_1$, $R_2$, $R_3$ and $R_4$, which are identical or different, preferably represent an alkyl comprising from 1 to 12 carbon atoms, more preferably an alkyl comprising from 1 to 8, in particular from 1 to 6, carbon atoms, it being possible for these alkyls optionally to form a heterocycle with the two oxygen atoms and the boron atom to which they are respectively bonded.

More preferably still, $R_1$ and $R_2$, on the one hand, $R_3$ and $R_4$, on the other hand, form a heterocycle with the two oxygen atoms and the boron atom to which they are respectively bonded.

This heterocycle more preferably corresponds to one of the three formulae (a), (b) or (c) which follow:

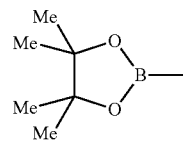

(a)

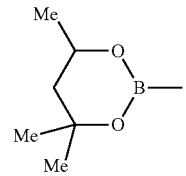

(b)

-continued

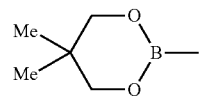

(c)

This heterocycle corresponds, more preferably still, to the formula (a) above.

According to another more particular embodiment of the invention, the boron atom borne by each benzene nucleus is located in the para position with respect to the oxygen of the oxazine ring.

Thus, according to particularly preferred embodiments of the invention, the borated benzoxazine of the invention corresponds to one of the formulae (A-1-a) to (A-5-a) below:

represent an integer, preferably an integer such that Z (in this instance aliphatic) comprises from 1 to 20, more preferably from 1 to 16, carbon atoms (and optionally at least one heteroatom chosen from O, S and P).

According to an even more particularly preferred embodiment of the invention, the borated benzoxazine of the invention corresponds to the formula (A-4-a) above.

(A-1-a)

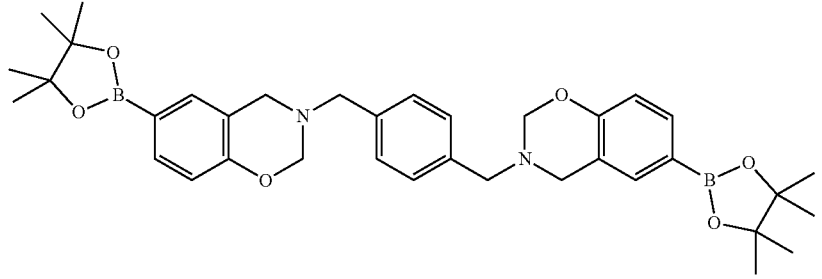

(A-2-a)

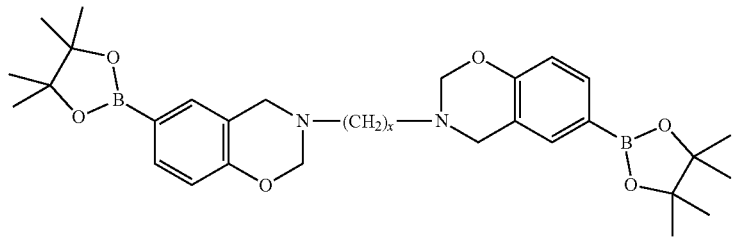

(A-3-a)

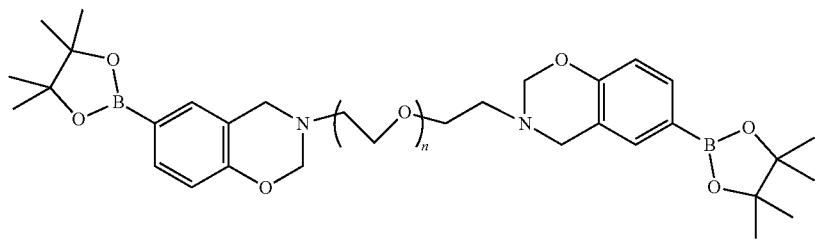

(A-4-a)

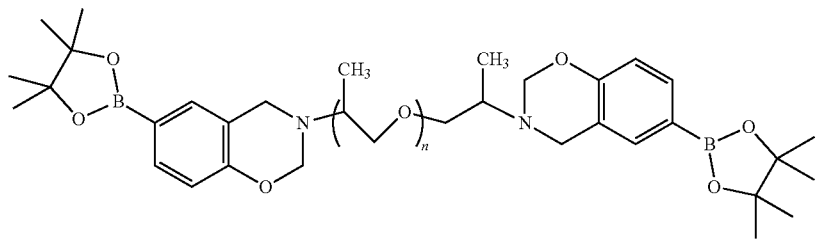

(A-5-a)

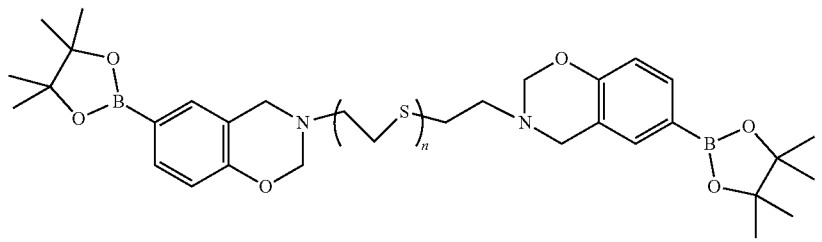

In the formulae (A-2) to (A-5) above, in particular in the formulae (A-2-a) to (A-5-a) above, the symbols "x" and "n"

Each benzene nucleus of the two oxazine rings of the Monomer M of the invention thus bears a boron atom.

Moreover, in this monomer of formula (A), one or more hydrogen atoms of at least one or of each benzene nucleus of the two oxazine rings can be substituted (or not) by various substituents, for example by functional groups capable of further promoting the adhesion of the polymer to the metal and/or to the rubber.

As said above, according to a first particularly preferred embodiment, Z comprises an aromatic group comprising from 6 to 30, more preferably from 6 to 20, carbon atoms.

Thus, FIG. 4 illustrates a possible scheme for the synthesis, under heat input and with removal of water, starting from a brominated phenol, paraformaldehyde and a specific diamine of the aromatic type (p-xylylenediamine), of a particular brominated benzoxazine, of formula (Ao-1), which can be used as starting compound (Monomer denoted Mo-1) in the subsequent synthesis of a borated benzoxazine in accordance with the invention corresponding to the first particularly preferred embodiment set out above.

According to another particularly preferred embodiment, Z represents a (poly)alkylene (or alkylidene) sequence comprising from 1 to 16, more particularly from 1 to 12, carbon atoms, it being possible for such a sequence to be optionally interrupted by at least one heteroatom chosen from O and S.

Thus, FIG. 5 illustrates a possible scheme for the synthesis, under heat input and with removal of water, starting from the brominated phenol, paraformaldehyde and another specific diamine, this time of the aliphatic type (polyethylenediamine), of another example of particular brominated benzoxazine, of formula (Ao-2), which can be used as starting monomer (Monomer denoted Mo-2) in the synthesis of a borated benzoxazine in accordance with the invention corresponding to the other particularly preferred embodiment set out above. It is noted that Z represents in this instance a —(CH$_2$)$_x$— group in which the symbol "x" represents an integer, preferably from 1 to 12. Such a synthesis will be described in more detail in the implementational examples which follow (FIG. 19).

FIGS. 6, 7 and 8 illustrate three other possible schemes for the synthesis, still starting from a halogenated phenol and paraformaldehyde, on the one hand, and, on the other hand, different specific diamines, all of the aliphatic type, of other examples of particular brominated benzoxazines, of respective formulae (Ao-3), (Ao-4) and (Ao-5), which can all be used as starting monomer (Monomers denoted Mo-3, Mo-4 and Mo-5) in the subsequent synthesis of other examples of borated benzoxazines according to the invention, of respective formulae (A-3), (A-4) and (A-5). In these formulae, the symbol "n" represents an integer, preferably an integer such that Z (in this instance aliphatic) comprises from 1 to 20, more preferably from 1 to 16, carbon atoms (and optionally at least one heteroatom chosen from O, S and P).

In FIG. 6, the repetition of the [—CH$_2$—CH$_2$—O—] (polyethylene oxide) units on the bonding group Z is capable of resulting in polybenzoxazines of high crystallinity, while, in FIG. 7, the presence of the methyl groups (polypropylene oxide) on Z makes it possible to reduce the reactivity of the two amine end groups and to result in polybenzoxazines of reduced crystallinity. In FIG. 8, the presence on the spacer Z of the sulfur atom (heteroatom) in the [—CH$_2$—CH$_2$—S—] (polyethylene thioether) repeating entities is capable of further improving the adhesion of the polybenzoxazine to the metal. Thus, it may be seen that the structure of the Z group can be widely modified with the aim of adjusting the properties of the borated benzoxazine of the invention and those of the final polymer (polybenzoxazine). This constitutes a major advantage of the present invention.

FIG. 9 now illustrates a scheme for the synthesis of an example of borated benzoxazine in accordance with the invention, of particular formula (A-1), by borylation of the brominated benzoxazine of preceding formula (Ao-1) using a diboronic ester or acid, this borated benzoxazine according to the invention being able to be used as starting monomer (Monomer denoted M-1) in the synthesis of a polybenzoxazine according to the process of the invention.

FIGS. 10, 11, 12 and 13 give various other schemes for the synthesis of other examples of borated benzoxazines in accordance with the invention, of respective formulae (A-2), (A-3), (A-4) and (A-5), by borylation of the brominated benzoxazines of preceding respective formulae (Ao-2), (Ao-3), (Ao-4) and (Ao-5), using a diboronic ester or acid, these borated benzoxazines according to the invention being able to be used as starting monomers (Monomers denoted M-2, M-3, M-4 and M-5 respectively) in the synthesis of other polybenzoxazines according to the process of the invention.

The borated benzoxazine in accordance with the invention of formula (A) described above is intended in particular (as first Monomer "M") for the synthesis of a polybenzoxazine by polycondensation, in particular by polycondensation with at least (as second monomer "N") one other benzoxazine, of the brominated type, having the formula (Br representing, of course, a bromine atom):

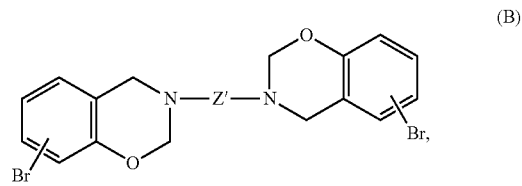

(B)

in which formula (B) Z', which is identical to or different from Z defined above, represents an at least divalent, aliphatic, cycloaliphatic or aromatic, bonding group comprising at least one carbon atom and optionally at least one heteroatom chosen from O, S and P.

FIG. 14 represents a general scheme for the synthesis of a polybenzoxazine (Polymer denoted "P") by polycondensation of the borated benzoxazine according to the invention of formula (A) of FIG. 3 (Monomer M), as first monomer, with, as second monomer, the other monomer of generic formula (B) which is, in this instance, a benzoxazine (Monomer denoted "N") of the brominated type.

Moreover, as for the preceding formula (A), one or more hydrogen atoms of at least one or of each benzene nucleus of the two oxazine rings of the formula (B) above might be substituted by a single or several substituents, which are identical or different, for example by functional groups capable of promoting the adhesion of the polymer to the metal and/or to the rubber.

Z', which is identical to or different from Z, has the same general definition and the same preferred definitions as those indicated above for Z.

In particular, according to a first particularly preferred embodiment, Z' comprises an aromatic group comprising from 6 to 30, more preferably from 6 to 20, carbon atoms (and optionally at least one heteroatom chosen from O, S and P).

According to another particularly preferred embodiment, Z' represents a (poly)alkylene sequence comprising from 1 to 20, more particularly from 1 to 16, in particular from 1 to 12, carbon atoms, and optionally at least one heteroatom chosen from O and S.

Thus, according to a particularly preferred embodiment of the invention, the brominated benzoxazine which can be used (as monomer "N") corresponds to one of the formulae below (in which "x" and "n" have already been defined above):

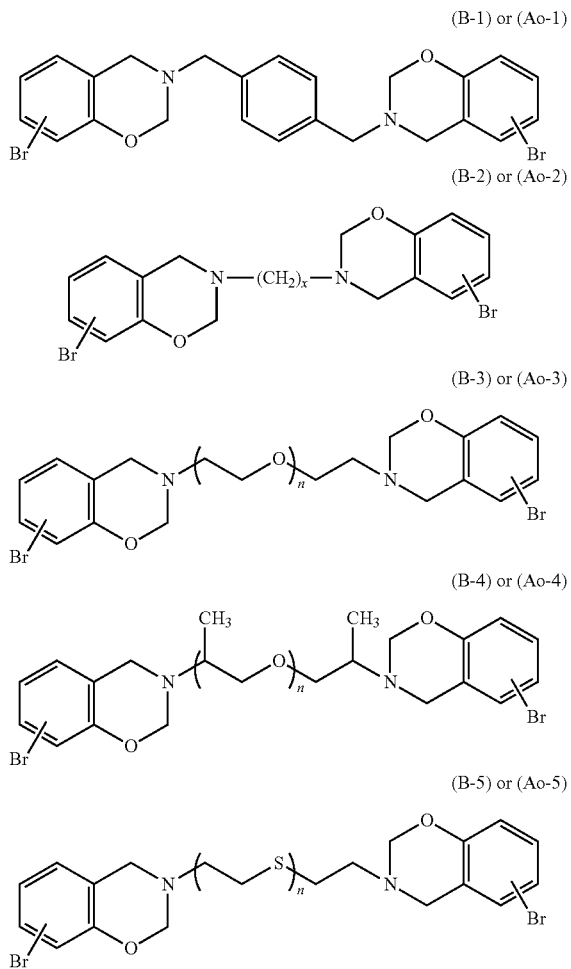

When Z (formula A) and Z' (formula B) are identical, it should be noted that the formulae (B-1) to (B-5) above are, of course, equivalent to the preceding formulae (Ao-1) to (Ao-5) respectively, precisely those of the starting monomers (Mo-1 to Mo-5 respectively) used in the synthesis of the borated benzoxazines of the invention of formulae (A-1) to (A-5) described above.

In other words, in the process in accordance the invention, which constitutes an advantageous embodiment thereof, the starting monomers used in the synthesis of the borated benzoxazines of the invention may also be able to be used as second monomer in the synthesis of polybenzoxazines.

According to another preferred embodiment of the invention, in the general formula (B) and the more particular formulae (B-1) to (B-5) above, the bromine atom borne by each benzene nucleus of the two oxazine rings is located in the para position with respect to the oxygen of the oxazine ring.

FIG. 15 reproduces, by way of example, a particular scheme for the synthesis of a particular polybenzoxazine polymer (Polymer denoted P-1), starting from the specific borated benzoxazine according to the invention of formula (A-1-a) (Monomer M-1-a) and another benzoxazine of generic formula (B-1) (Monomer denoted N-1) of the brominated type. It is noted that Z' represents in this instance a —(CH$_2$)— group in which the symbol "y" represents an integer, preferably from 1 to 12. Such a synthesis will be described in more detail in the implementational examples which follow.

FIGS. 16 and 17 reproduce, by way of examples, two other possible schemes for the synthesis of particular polybenzoxazine polymers (Polymers denoted P-2 and P-3 respectively), starting from specific borated benzoxazines according to the invention of respective formulae (A-2-a) and (A-4-a) (Monomers M-2-a and M-4-a) and this other benzoxazine of generic formula (B-1) (Monomer denoted N-1) of the brominated type.

As reproduced in FIG. 18, the benzoxazine in accordance with the invention of formula (A) is thus intended in particular for the synthesis of a polybenzoxazine (Polymer denoted "P") comprising repeating structural entities comprising at least one unit corresponding to the formula (I) (before opening of the oxazine rings) or the formula (II) (after opening of the rings) below:

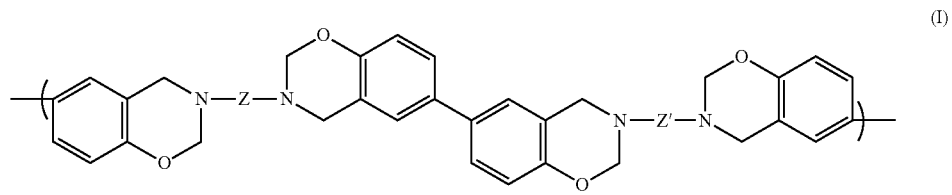

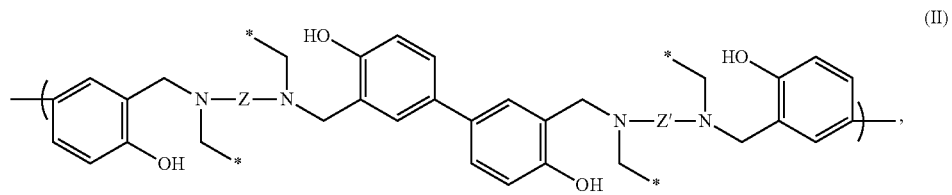

in which formulae (I) and (II) Z and Z' have the main definitions and the preferred definitions already given above for the borated benzoxazine of the invention and its starting brominated benzoxazine.

Polymer should be understood in this instance as meaning any homopolymer or copolymer, in particular block copolymer, with repeating structural entities comprising at least one unit of formula (I) or (II) above; this polymer can, of course, comprise both units of formula (I) and units of formula (II).

In the formula (II) above, a person skilled in the art will immediately understand that the two symbols "*" (which are identical or different) represent any attachment of the unit to a carbon atom or to a heteroatom (preferably chosen from O, S, N and P), which attachment or bond results from the opening of the oxazine rings.

FIGS. 19, 20 and 21 reproduce particular examples of the synthesis successively of a specific brominated dibenzoxazine, then of a borated benzoxazine in accordance with the invention, starting from this brominated dibenzoxazine, and finally of a polymer (polybenzoxazine) by polycondensation of these two (brominated and borated) benzoxazines.

More specifically, FIG. 19 reproduces the scheme for the synthesis, under heat input and with removal of water, starting from a brominated phenol (compound 1), paraformaldehyde (compound 3) and a specific aliphatic diamine (compound 2), of a particular brominated dibenzoxazine of formula (Ao-6) (Monomer denoted Mo-6) which will be used in the synthesis of a borated benzoxazine in accordance with the invention (benzoxazine of FIG. 20 which follows).

FIG. 20 gives the specific scheme for the synthesis of a borated benzoxazine in accordance with the invention, of formula (A-6), by borylation of the brominated benzoxazine of preceding formula (Ao-6) using a diboronic ester (bispinacol ester of boric acid) (compound 4). It is noted that the formula (A-6) of this example corresponds to the preceding formula (A-2-a) in which "x" is equal to 8.

Finally, FIG. 21 describes the specific method of synthesis of an example of particular polybenzoxazine polymer (Polymer denoted P-4) by polycondensation of the preceding borated benzoxazine according to the invention of formula (A-6) (Monomer M-6) with, as second monomer, its equivalent starting benzoxazine of formula (Ao-6) (Monomer Mo-6) of the brominated type. In this example, it is noted in particular that, according to a preferred embodiment of the invention already described, the boron atom in the Monomer M-6, just like the bromine atom in the Monomer Mo-6, are each located in the para position with respect to the oxygen of each oxazine ring.

This polybenzoxazine P-4, or more precisely at least a portion of its repeating entities, has been represented in FIG. 21, before (Formula (I-4); Polymer P-4) and after (Formula (II-4); Polymer P-4') opening of its oxazine rings following a sufficient heat input.

In order to complete this detailed description of the invention, FIGS. 22, 23 and 24 reproduce other particular examples of the synthesis successively of another specific brominated dibenzoxazine, then of a borated benzoxazine in accordance with the invention, starting from this brominated dibenzoxazine, and finally of a polymer (polybenzoxazine) by polycondensation of these two (brominated and borated) benzoxazines.

More specifically, FIG. 22 reproduces the scheme for the synthesis, starting from a brominated phenol (compound 1), paraformaldehyde (compound 3) and another specific diamine, in this instance of aromatic type (compound 5), of a particular brominated dibenzoxazine of formula (Ao-7) (Monomer denoted Mo-7) which can be used in the synthesis of a borated benzoxazine in accordance with the invention (benzoxazine of FIG. 23 which follows).

FIG. 23 gives the specific scheme for the synthesis of a borated benzoxazine in accordance with the invention, of formula (A-7), by borylation of the brominated benzoxazine of preceding formula (Ao-7) using a diboronic ester (bispinacol ester of boric acid) (compound 4), this borated benzoxazine according to the invention being able to be used ultimately as starting monomer (Monomer denoted M-7) in the synthesis of a polybenzoxazine (polymer denoted P-5 in FIG. 24 which follows). It is noted that the formula (A-7) of this example corresponds to the formula (A-1-a) described above.

Finally, FIG. 24 describes the specific method for the synthesis of an example of particular polybenzoxazine polymer (Polymer P-5) starting from the preceding specific borated benzoxazine according to the invention of formula (A-7) (Monomer M-7) and from its equivalent starting benzoxazine of formula (Ao-7) (Monomer Mo-7) of the brominated type, and also this same polybenzoxazine (Polymer denoted P-5') once its oxazine rings have been opened after heat treatment of the Polymer P-5.

Typically, the polybenzoxazine resulting from the benzoxazine compound of the invention can comprise from ten to several hundred, preferably from 50 to 300, structural entities having units of formula (I) and/or (II), in particular structural entities as represented by way of examples in FIGS. 14 to 18, 21 and 24.

This polybenzoxazine resulting from the benzoxazine of the invention can advantageously be used, as adhesion primer or as sole adhesive layer, in order to coat a metal substrate, at the very least a substrate of which at least the surface is at least partially metallic, and to cause the substrate to adhere to rubber. It can very particularly be used on any type of metal reinforcer, such as, for example, a thread, a film or a cord made of steel, in particular of carbon steel, intended in particular to reinforce a matrix of unsaturated rubber, such as natural rubber. Any known adhesive system, for example a conventional textile adhesive of the RFL (resorcinol/formaldehyde latex) type, can also be used to cause the rubber to adhere to the polybenzoxazine layer. A person skilled in the art will readily understand that the connection between the metal substrate provided with its polybenzoxazine layer and the rubber layer with which it is in contact will be definitively provided during the final curing (crosslinking) of the rubber article in question.

6. IMPLEMENTATIONAL EXAMPLES OF THE INVENTION

In the present patent application, unless expressly indicated otherwise, all the percentages (%) shown are % by weight.

The tests which follow describe:
first of all, the manufacture of a starting brominated benzoxazine (Monomer Mo-7) of formula (Ao-7):

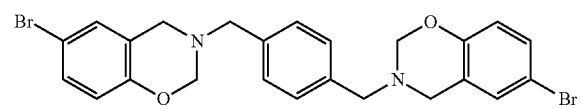 [SMILES: Brc1ccc2c(c1)CN(Cc1ccc(CN3COc4ccc(Br)cc4C3)cc1)CO2]

then the synthesis, starting from the latter, of the borated benzoxazine in accordance with the invention (Monomer M-7) of formula (A-7):

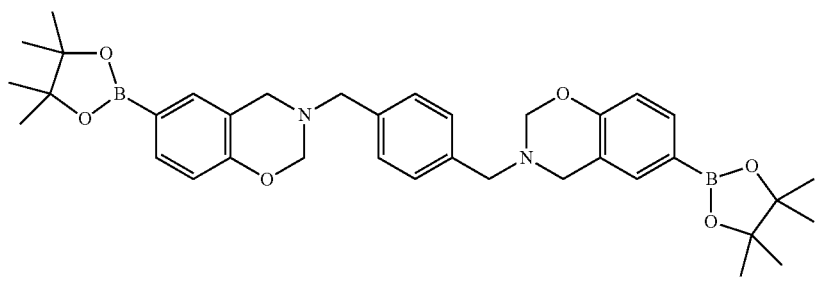

then the synthesis, according to a process in accordance with the invention, by polycondensation of the monomers Mo-7 and M-7, of a polybenzoxazine (Polymer P-5) of formula (I-5):

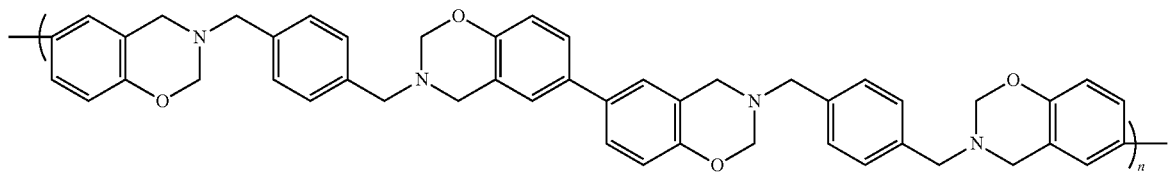

finally, adhesion tests are carried out in order to illustrate the excellent adhesive performance of this polybenzoxazine (Polymer P-5) resulting from the compound (Monomer M-7) of the invention.

5.1. Synthesis of the Starting Brominated Benzoxazine (Monomer Mo-7)

For this synthesis, a 250-ml three-necked round-bottomed flask, equipped with a thermometer, a nitrogen inlet, a magnetic stirrer and a condenser, is provided.

The synthesis is carried out according to the procedure diagrammatically represented in FIG. 22, as explained in detail below, starting from three compounds: a halogenated phenol (compound 1; 4-bromophenol; Aldrich product B75808), an aromatic diamine (compound 5; p-xylylenediamine; TCI Europe product D1018) and paraformaldehyde (compound 3; Aldrich product 158127), in the presence of two solvents (anhydrous toluene and anhydrous ethanol).

Compound 1 (2 eq., 10.38 g, i.e. 60 mmol) and then ethanol (51 ml) are poured into the round-bottomed flask. The presence of ethanol is important in this instance, preventing the formation of an unstable triazine-type intermediate product. Compound 5 (1 eq., 4.13 g, i.e. 30 mmol), compound 3 (4 eq., 3.60 g, i.e. 120 mmol) and finally the toluene (102 ml) are subsequently introduced with stirring. The reaction medium is heated (approximately 75° C.) at reflux for 51 h and then the solvents and volatile residues are distilled off at 110° C. (under vacuum of 1 mbar) for evaporation. The final product is subsequently washed (100 ml methanol) and dried; a yellow-coloured powder is thus obtained.

This powder is placed in methanol (100 ml per 15 g of powder) and the mixture is heated at reflux (65° C.) for 30 min. The solution is then left to cool to ambient temperature (approximately 20° C.) for crystallization of the monomer. The solid product obtained is isolated by filtration (Büchner filter). A white-coloured powder is thus obtained, after drying in an oven under vacuum at 50° C. overnight (reaction yield equal to approximately 82%).

The $^1$H NMR spectrum (500 MHz) of the Monomer Mo-7 thus synthesized, dissolved in chloroform, confirmed its chemical structure, with the following results: 3.89 (s, 4H), 3.94 (s, 4H), 4.87 (s, 4H), 6.70 (s, 1H), 6.72 (s, 1H), 7.06 (s, 2H), 7.23 (s, 2H), 7.32 (s, 4H).

5.2. Synthesis of the Borated Benzoxazine in Accordance with the Invention (Monomer M-7)

The synthesis is carried out according to the procedure diagrammatically represented in FIG. 23, as explained in detail below, starting from two compounds: the starting monomer Mo-7 (dried beforehand under vacuum at 60° C. overnight) and a diboronic heterocycle (compound 4), available commercially (CAS 73183-34-3; Sigma Aldrich product No. 697230; purity 99%), which is the bispinacol ester of diboronic acid, of formula:

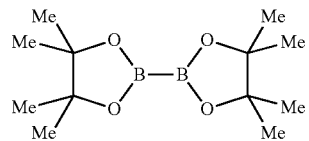 [SMILES: CC1(C)OB(B2OC(C)(C)C(C)(C)O2)OC1(C)C]

This heterocycle clearly corresponds to the abovementioned formula (a) in which $R_1$, $R_2$, $R_3$ and $R_4$ each represent a methyl ("Me") group.

The synthesis is carried out in a 25-ml three-necked round-bottomed flask, equipped with a folding skirted stopper, with a nitrogen inlet, with a thermometer, with a magnetic stirrer and with a condenser, everything being in the presence of anhydrous DMF (N,N-dimethylformamide; Acros Organics product No. 326871000) solvent and of anhydrous potassium acetate (Sigma Aldrich product No. 791733) dried beforehand under vacuum at a temperature of 100° C. for 12 h.

The apparatus is dried under vacuum using a hot air gun until the thermometer reaches a temperature of at least 100° C. in the reaction round-bottomed flask. Everything is left to cool to ambient temperature (20° C.) and then the apparatus is placed under a stream of nitrogen throughout the synthesis.

200 mg of monomer Mo-7, 6 ml of DMF, 111 mg of potassium acetate and 211 mg of Compound 4 are then successively introduced into the round-bottomed flask with stirring. A solution, in 2 ml of DMF, of 16.5 mg of Pd(dppf)Cl$_2$ catalyst (Sigma Aldrich product No. 697230), weighed in a glovebox under a nitrogen stream, is then injected using a syringe.

The reaction mixture is heated at 80° C. for 40 h, is decanted into a 50 ml round-bottomed flask and then the DMF solvent is distilled at 95° C. under 35 mbar using a rotary evaporator. The distillation residue is left to cool to ambient temperature (20° C.) and then under stirring with 16 ml of deionized water for 10 min.

The suspension thus obtained is centrifuged at 10 000 revolutions/min for 5 min. The product obtained is subsequently decanted into a receptacle containing 40 ml of chloroform and 10 ml of deionized water, and the combined mixture is stirred at ambient temperature for 10 min. The aqueous phase is extracted twice with 40 ml of chloroform, the organic phase is then dried over sodium sulfate and filtered, and finally the chloroform is evaporated using a rotary evaporator. The product thus obtained is purified by silica gel chromatography and then eluted with an ethyl acetate/cyclohexane (1:3) mixture.

The $^1$H NMR spectrum (500 MHz) of the final product (Monomer M-7) thus synthesized, dissolved in CD$_2$Cl$_2$, confirmed its chemical structure, with the following results:

1.31 (s, 24H), 3.89 (s, 4H), 3.97 (s, 4H), 3.89 (s, 4H), 3.97 (s, 4H), 4.90 (s, 4H), 6.77 (d, 2H), 7.31 (m, 4H), 7.37 (m, 2H), 7.51 (d, 1H), 7.53 (d, 1H).

5.3. Synthesis of the Polybenzoxazine (Polymer P-5)

This synthesis is carried out according to the procedure diagrammatically represented in FIG. 24, as described in detail below, starting from two monomers: the benzoxazine of the invention obtained in the preceding stage (Monomer M-7) and its starting brominated benzoxazine (Monomer Mo-7), everything being in the presence of potassium carbonate (K$_2$CO$_3$; Riedel-de Haën product No. 31245) and of (anhydrous) DMF (N,N-dimethylformamide; Acros Organics product No. 326871000) solvent. The two monomers (Mo-7 and M-7) are dried beforehand under vacuum at 50° C. overnight, and likewise for the potassium carbonate but at a temperature of 150° C.

The synthesis is carried out in a 50-ml three-necked round-bottomed flask, equipped with a folding skirted stopper, with a nitrogen inlet, with a thermometer, with a magnetic stirrer and with a condenser. The apparatus is dried under vacuum using a hot air gun until the thermometer reaches a temperature of at least 100° C. in the reaction round-bottomed flask. Everything is left to cool to ambient temperature (20° C.) and then the apparatus is placed under a stream of nitrogen throughout the synthesis.

The Monomer M-7 (1 eq., 0.106 g, i.e. 0.2 mmol) of formula (A-7) and then the Monomer Mo-7 of formula (Ao-7) (1 eq., 0.125 g, i.e. 0.2 mmol) are successively introduced into the round-bottomed flask with stirring. 10 ml of DMF (solvent of both monomers) and then, as base, K$_2$CO$_3$ (5 eq., 0.149 g, i.e. 1 mmol) are subsequently added. A solution, in 4 ml of DMF, of 2.9 mg of Pd(dppf)Cl$_2$ catalyst, weighed in a glovebox under a nitrogen stream, is then injected using a syringe.

The reaction mixture is heated at 80° C. for 48 h and is then left to cool to ambient temperature; the mixture is finally poured into 50 ml of deionized water and everything is vigourously stirred (magnetic bar) at 20° C. for 30 min; during this washing operation, in order to extract the potassium carbonate, acid (1% HCl) is added dropwise until neutral pH is reached. The precipitate thus obtained is isolated by filtration (Büchner filter) and washed (twice) with 50 ml of distilled water, then dried under vacuum at 40° C. overnight (approximately 12 h).

The Polymer P-5 of FIG. 24 was thus obtained, as attested to by the $^1$H NMR analysis (500 MHz) in the solvent d9-DMA, which gave the following results: 3.95 (s, 4H), 4.03 (s, 4H), 4.94 (s, 4H), 6.80-6.82 (d, 2H), 6.87-6.89 (d, 2H), 7.28-7.29 (m, 4H), 7.36-7.37 (m, 3H), 7.43-7.46 (m, 2H).

This Polymer P-5, in the form of a beige-coloured powder, was also analysed by DSC (Differential Scanning Calorimetry) between −80° C. and +320° C. along a gradient of 10° C./min (Mettler Toledo "822-2" DSC device; nitrogen atmosphere). The analysis showed, in the first pass (between −80° C. and +320° C.), an exothermicity (corresponding to the opening of the oxazine rings and to the crosslinking of the polymer) above 200° C., with a maximum at approximately 260° C. During the second and third DSC passes, carried out between −80° C. and +320° C., no apparent glass transition (Tg) was visible.

5.4. Test of Adhesion in a Metal/Rubber Composite

A portion (325 mg) of the Polymer P-5 prepared above was dissolved in 8 ml of DMPU (1,3-dimethyl-3,4,5,6-tetrahydro-2(1H)-pyrimidinone; Sigma Aldrich product 41661) with 10% by weight of "DY 9577 ES" accelerator (Huntsman product), this being in order to form a solution, a fraction (0.6 ml) of which was subsequently deposited uniformly on a brass tape (film) having dimensions of 10 cm×2.5 cm and a thickness of 0.5 mm; the assembly was placed in an oven at 175° C. (air ventilation) for 5 min and then for an additional 5 min at 230° C. under vacuum in order, on the one hand, to remove any trace of solvent and, on the other hand, to at least partially (that is to say, completely or partially) open the oxazine rings of the polymer, this last stage being accompanied by a pronounced change in colour of the polymer, which changes to dark orange.

After cooling to ambient temperature, the tape provided at the surface with its thin (thickness 5 to 10 µm) layer of polybenzoxazine thus formed was subsequently subjected to a conventional two-stage adhesive coating operation (two baths adhesive coating), first of all by immersion in a first aqueous bath (approximately 94% water) based on epoxy resin (polyglycerol polyglycidyl ether, approximately 1%) and on isocyanate compound (caprolactam-blocked isocyanate compound, approximately 5%), which first adhesive coating stage is followed by a drying (2 min at 100° C.) and then by a heat treatment (5 min at 200° C.). The tape thus treated was then immersed in a second aqueous bath of RFL adhesive (approximately 81% by weight of water) based on resorcinol (approximately 2%), on formaldehyde (approximately 1%) and on a rubber latex (approximately 16% of NR, SBR and VP-SBR rubbers); finally, it was dried in an oven at 130° C. for 2 min and then heat treated at 200° C. for 5 min.

The brass tape thus coated with the polybenzoxazine film and then coated with adhesive was subsequently placed between two layers of conventional rubber composition for a belt reinforcement of a passenger vehicle tyre, which composition is based on natural rubber, on carbon black and silica as filler and on a vulcanization system (sulfur and sulfenamide accelerator); this composition was devoid of cobalt salt. The metal/rubber composite test specimen thus prepared was then placed under a press and everything was cured (vulcanized) at 150° C. for 30 min under a pressure of 20 bar.

After vulcanization of the rubber, excellent adhesive bonding between the rubber matrix and the metal tape was obtained, despite the absence of cobalt salt in the rubber matrix; this is because, during peel tests (at 20° C.), it was found that the failure occurred systematically in the rubber matrix itself and not at the interphase between metal and rubber. Other adhesive bonding tests were carried out on a bright (uncoated) steel tape; they themselves also revealed an excellent adhesion to the rubber (systematic failure in the rubber matrix).

In conclusion, the borated benzoxazine according to the invention makes possible the synthesis of polymers giving the metal reinforcers the major advantage of being able subsequently to be adhesively bonded to rubber matrices using simple textile adhesives, such as RFL adhesives, or else directly (that is to say, without employing such adhesives) to these rubber matrices, for example when the latter contain appropriate functionalized unsaturated elastomers, such as epoxidized elastomers.

Thus, use may be made of metal reinforcers coated or not coated with adhesive metal layers, such as brass, and also of surrounding rubber matrices devoid of metal salts, in particular of cobalt salts.

Moreover, this constituting a significant advantage in comparison with the other known polymers described in the introduction to the present document, the polybenzoxazines resulting from the borated benzoxazines of the invention have the remarkable ability, at high temperature, to open their oxazine rings and to thus result in a thermosetting polyphenol resin structure. This confers a better thermal stability on them. Finally, their specific microstructure makes it possible, very advantageously, to adjust the flexibility of the molecule according to the particular applications targeted.

The invention claimed is:

1. A borated benzoxazine compound corresponding to the formula:

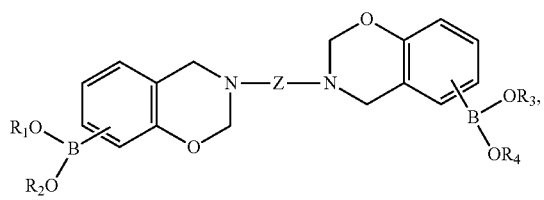

(A)

in which:
  Z represents an at least divalent aliphatic, cycloaliphatic or aromatic bonding group comprising at least one carbon atom and optionally at least one heteroatom chosen from O, S and P; and
  $R_1$, $R_2$, $R_3$ and $R_4$, which are identical or different, represent hydrogen or an alkyl comprising from 1 to 12 carbon atoms, it being possible for $R_1$ and $R_2$, or $R_3$ and $R_4$, or both $R_1$ and $R_2$, and $R_3$ and $R_4$, optionally to form a heterocycle with the two oxygen atoms and the boron atom to which they are respectively bonded.

2. The borated benzoxazine compound according to claim 1, wherein Z comprises an aromatic group comprising from 6 to 30 carbon atoms.

3. The borated benzoxazine compound according to claim 2 corresponding to the formula (A-1):

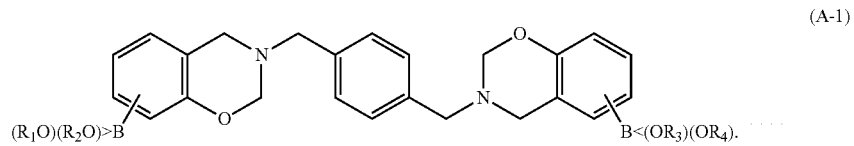

(A-1)

4. The borated benzoxazine compound according to claim 1, wherein Z represents an aliphatic group comprising from 1 to 20 or a cycloaliphatic group comprising from 3 to 20 and optionally at least one heteroatom chosen from O and S.

5. The borated benzoxazine compound according to claim 4, wherein Z represents a (poly)alkylene sequence comprising from 1 to 20 carbon atoms and optionally at least one heteroatom chosen from O and S.

6. The borated benzoxazine compound according to claim 5 corresponding to one of the formulae (A-2) to (A-5):

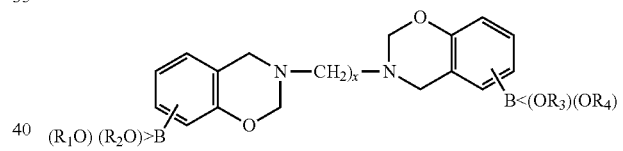

(A-2)

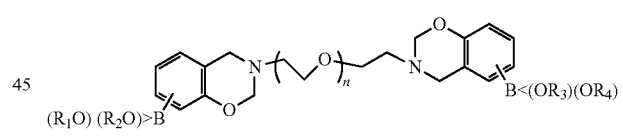

(A-3)

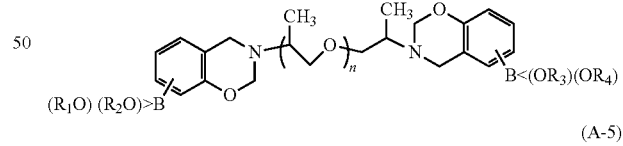

(A-4)

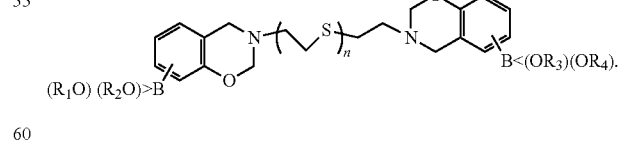

(A-5)

7. The borated benzoxazine compound according to claim 1, wherein $R_1$, $R_2$, $R_3$ and $R_4$, which are identical or different, represent an alkyl.

8. The borated benzoxazine compound according to claim 7, wherein the alkyl comprises from 1 to 8 carbon atoms.

9. The borated benzoxazine compound according to claim 1, wherein both $R_1$ and $R_2$, and $R_3$ and $R_4$, form a heterocycle with the two oxygen atoms and the boron atom to which they are respectively bonded.

10. The borated benzoxazine compound according to claim 9, wherein each heterocycle corresponds to one of the formulae (a), (b) or (c) below:

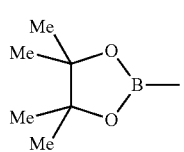
(a)

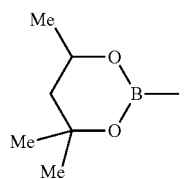
(b)

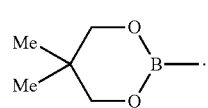
(c)

11. The borated benzoxazine compound according to claim 10, wherein each heterocycle corresponds to the formula (a).

12. The borated benzoxazine compound according to claim 1, wherein the boron atom borne by each benzene nucleus of the two oxazine rings is located in the para position with respect to the oxygen of the oxazine ring.

13. The borated benzoxazine compound according to claim 12 corresponding to one of the formulae (A-1-a) to (A-5-a) below:

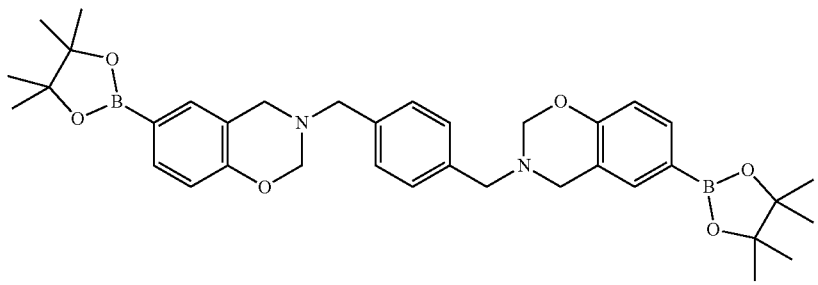
(A-1-a)

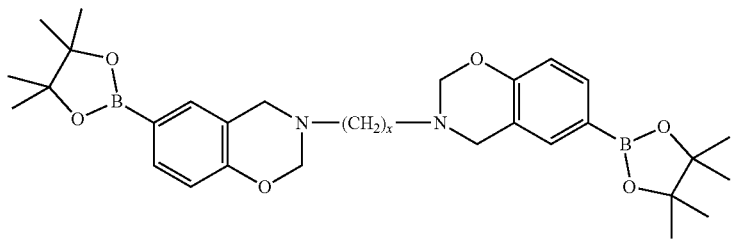
(A-2-a)

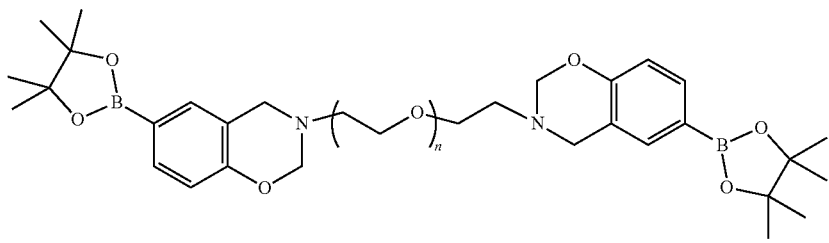
(A-3-a)

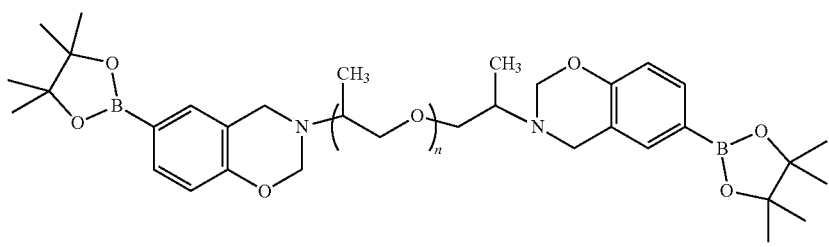
(A-4-a)

-continued (A-5-a)

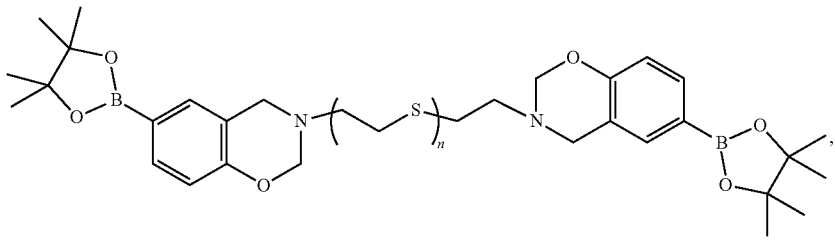

in which the symbols x and n represent an integer such that Z comprises from 1 to 20 carbon atoms.

14. A process for the synthesis of a polybenzoxazine comprising the step of:
polycondensating a borated benzoxazine compound corresponding to the formula:

(A)

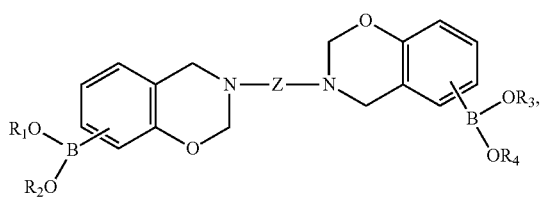

in which:
Z represents an at least divalent aliphatic, cycloaliphatic or aromatic bonding group comprising at least one carbon atom and optionally at least one heteroatom chosen from O, S and P; and
$R_1$, $R_2$, $R_3$ and $R_4$, which are identical or different, represent hydrogen or an alkyl comprising from 1 to 12 carbon atoms, it being possible for $R_1$ and $R_2$, or $R_3$ and $R_4$, or both $R_1$ and $R_2$, and $R_3$ and $R_4$, optionally to form a heterocycle with the two oxygen atoms and the boron atom to which they are respectively bonded;
wherein the borated benzoxazine compound corresponding to the formula (A), as a first monomer, is polycondensated with, as second monomer, at least a brominated benzoxazine having the formula (B):

(B)

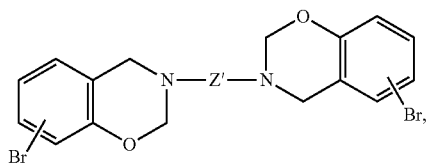

in which Z', which is identical to or different from Z, represents an at least divalent, aliphatic, cycloaliphatic or aromatic, bonding group comprising at least one carbon atom and optionally at least one heteroatom chosen from O, S and P.

15. The process according to claim 14, wherein Z' comprises an aromatic group comprising from 6 to 30 carbon atoms.

16. The process according to claim 14, wherein Z' represents a (poly)alkylene sequence comprising from 1 to 20 carbon atoms.

17. A borated benzoxazine compound corresponding to the formula:

(A)

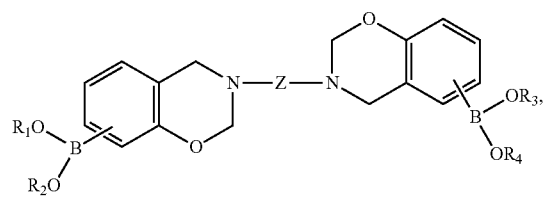

in which:
Z represents an aliphatic, cycloaliphatic or aromatic bonding group comprising at least one carbon atom and optionally at least one heteroatom chosen from O, S and P; and
$R_1$, $R_2$, $R_3$ and $R_4$, which are identical or different, represent hydrogen or an alkyl comprising from 1 to 12 carbon atoms, it being possible for $R_1$ and $R_2$, or $R_3$ and $R_4$, or both $R_1$ and $R_2$, and $R_3$ and $R_4$, optionally to form a heterocycle with the two oxygen atoms and the boron atom to which they are respectively bonded.

* * * * *